(12) United States Patent
Kassab et al.

(10) Patent No.: US 8,992,444 B2
(45) Date of Patent: Mar. 31, 2015

(54) DEVICES, SYSTEMS, AND METHODS FOR DETERMINING ISOMETRIC AND ISOTONIC ACTIVITY OF LUMINAL ORGANS

(75) Inventors: Ghassan S. Kassab, Zionsville, IN (US); Xiao Lu, Zionsville, IN (US)

(73) Assignee: DTherapeutics, LLC, San Diego, CA (US)

( * ) Notice: Subject to any disclaimer, the term of this patent is extended or adjusted under 35 U.S.C. 154(b) by 796 days.

(21) Appl. No.: 12/727,909

(22) Filed: Mar. 19, 2010

(65) Prior Publication Data

US 2010/0222651 A1 Sep. 2, 2010

Related U.S. Application Data

(63) Continuation-in-part of application No. 11/919,469, filed as application No. PCT/US2006/016523 on May 1, 2006.

(60) Provisional application No. 60/675,908, filed on Apr. 29, 2005.

(51) Int. Cl.
*A61B 5/103* (2006.01)
*A61B 5/0488* (2006.01)
*A61B 5/02* (2006.01)
*A61B 5/03* (2006.01)
*A61B 5/00* (2006.01)

(52) U.S. Cl.
CPC ......... *A61B 5/04882* (2013.01); *A61B 5/02007* (2013.01); *A61B 5/036* (2013.01); *A61B 5/418* (2013.01); *A61B 2503/40* (2013.01)
USPC ........................................... 600/587; 600/36

(58) Field of Classification Search
USPC .................................................. 600/36, 587
See application file for complete search history.

(56) References Cited

PUBLICATIONS

Falloon et al. "In Vitro Perfusion Studies of Human Resistance Artery Function in Essential Hypertension" pp. 16-22, 11994. as submitted by applicant.*
Zhang et al. "Carbon monoxide producted by isolated arterioles attenuates pressure-induced vasoconstriction" Am J. Physiol. Heart Circ. 2001, pp. 350-358.*
PCT/US06/16523, PCT Search Report dated Nov. 30, 2006.
PCT/US06/16523, PCT Written Opinion dated Nov. 30, 2006.
(Continued)

*Primary Examiner* — Max Hindenburg
*Assistant Examiner* — Renee Danega
(74) *Attorney, Agent, or Firm* — Reichel IP LLP; Mark C. Reichel; Natalie J. Dean

(57) ABSTRACT

Devices, systems, and methods for determining isometric and isotonic activity of luminal organs. In an exemplary method for detecting a luminal organ response to mechanical stimulation of the present disclosure, the method comprises the steps of maintaining a luminal organ at a first internal pressure, increasing the first internal pressure of the luminal organ, and measuring a first organ parameter change in response to the increase in internal pressure. In an exemplary system for detecting a luminal organ response to mechanical stimulation of the present disclosure, the system comprises a first conduit having a proximal end, a distal end, and a lumen therethrough, the distal end sized and shaped to fit within a luminal organ, a pressure transducer, and at least one pressurized vessel capable of introducing a fluid into the lumen of the first conduit, wherein the first conduit, the pressure transducer, and the at least one pressurized vessel are either directly or indirectly coupled to one another so that a pressure of a fluid present within the first conduit can be measured using the pressure transducer.

25 Claims, 30 Drawing Sheets

(56) References Cited

PUBLICATIONS

Falloon, B.J., and Heagerty, A.M., In Vitro Perfusion Studies of Human Resistance Artery Function in Essential Hypertension, Hypertension, vol. 24, pp. 16-23, 1994.

Ohtaka, H. et al., Mechanical Properties of Porcine Intralobar Pulmonary Arteries, Journal of Applied Physiology, vol. 64, No. 4, pp. 1537-1545, Apr. 1, 1988.

Vanbavel, E. et al., Cannulation and Continuous Cross-sectional Area Measurement of Small Blood Vessels, Journal of Pharmacological Methods, vol. 24, No. 3, pp. 219-227, 1990.

Mulvany, M.J., Contractile Properties of Small Arterial Resistance Vessels in Spontaneously Hypertensive and Normotensive Rats, Circulation Research, Jul. 1977, vol. 41, No. 1, pp. 19-26.

European Search Report, European Patent Office, European Application Serisl No. 06751942,1, dated Nov. 17, 2009.

Supplementary European Search Report, European Patent Office, European Application Serial No. 06751942.1, dated Nov. 6, 2009.

* cited by examiner

DEVICES, SYSTEMS, AND METHODS FOR DETERMINING ISOMETRIC AND ISOTONIC ACTIVITY OF LUMINAL ORGANS

PRIORITY

This continuation-in-part application is related to, and claims the priority benefit of, U.S. Nonprovisional patent application Ser. No. 11/919,469, filed Oct. 29, 2007 which is related to, claims the priority benefit of, and is a U.S. national stage patent application of, and International Patent Application Serial No. PCT/US2006/016523, filed May 1, 2006, which is related to, and claims the priority benefit of, U.S. Provisional Patent Application Ser. No. 60/675,908, filed Apr. 29, 2005. The contents of each of these applications are hereby incorporated by reference in their entirety into this disclosure.

BACKGROUND

The present disclosure relates to the measurement of isometric and isotonic contraction of blood vessels and luminal organs. More particularly, the disclosure of the present application relates to devices, systems and methods for isometric and isotonic contraction of blood vessels and the determination of isometric and isotonic activity of luminal organs using an isovolumic myograph.

Vascular smooth muscle coils (VSMCs) modulate the tone of a blood vessel in response to neural, humoral or local hemodynamic stimuli. The VSMCs are important for autoregulation and largely determine the spatial and temporal distribution of blood flow in an organ. Thus, conditions that affect the proper function of VSMCs cause a variety of medical problems.

Many diseases, including hypertension, diabetes, heart failure and atherogenesis, show signs of impaired arterial vasoactivity. Hypertension, for example, is identified in relation to changes in the myogenic tone of the resistance arteries. The vasoactivity may be attenuated due to physiological (normal growth, exercise, pregnancy, etc.) or pathological remodeling (hypertension, hypertrophy, heart failure, etc.). The pressure-induced myogenic response (or tone) is initiated as a consequence of pressure-dependent modification of vascular smooth muscle wall tension and subsequent activation of mechanosensitive ion channels. Steady-state myogenic tone accounts for a substantial portion of the peripheral resistance and is an important determinant of arterial blood pressure. Although vasoconstriction and vasodilation are intrinsic properties of VSMC, they are often modulated by endothelium-derived vasoactive factors.

Because of the importance of maintaining proper vasoactivity in VSMC, various drugs are tested for their effects on such vasoactivity. Two of the tools used in such tests to identify vasoactivity in blood vessels include the wire and pressure myographs. A Medline search with keyword "wire myograph" or "pressure myograph" reveals 140 and 207 publications, respectively, from 1990 to the present having at least some reference to these conventional tools for testing vasoactivity. In pharmacology, these methods are used to understand the vasoreactivity and the dose-response relation of various agonists and antagonists.

Although the wire myograph method is used often for pharmacological experiments, it has a number of drawbacks, one being that it is far from physiological. The mechanical deformation of the ring is non-physiological and the cutting of the vessel produces some injury to the vessel which has a direct impact on the response of the vessel to the testing. In addition, the excision of rings and attachment to hooks cause injury and lead to a non-physiological geometry and loading. Furthermore, the reference length for the vessel ring is unknown and comparison between various vessels at various conditions is difficult to standardize.

The pressure myograph was developed to address some of the limitations of the wire myograph. In the pressure myograph, the vessel geometry and loading are typically more physiological. The pressure myograph method involves changes in pressure while recording the change in diameter under passive and active conditions. The method is substantially isobaric because the pressure is maintained constant during contraction. Since the radius changes during the test, which can change the wall stress (based on Laplace's equation), this method of mechanical testing is neither isometric nor isotonic, which in turn affects interpretation of the results. Unlike the high sensitivity of wire myograph that records tension, the pressure myograph records the diameter changes under isobaric conditions and hence is limited to small vessels that have substantial vasoactivity. Hence, there is currently no unified myograph that applies to small as well as large vessels under identical geometry, loading and testing protocols.

Vascular endothelial dysfunction is widely considered to be a consequence, a biomarker and a mediator of the adverse effects of cardiovascular risk factors. Endothelial dysfunction precedes the development of morphological atherosclerotic changes and can also contribute to lesion development and later clinical complications. Endothelial dysfunction has also been shown to be a predictor of adverse outcomes in patients with coronary artery disease. Ongoing efforts to identify and develop new drugs for the treatment of atherosclerosis depend on robust evaluation of vascular lesion pathology in preclinical models, a time consuming approach associated with significant variability of the data.

The stomach is largely dependent upon extrinsic nervous inputs arising from the central nervous system. These inputs regulate the smooth muscles and coordinate the digestive function of stomach by parasympathetic and sympathetic pathways. The excitatory neurotransmitters by efferent vagus fibers (mainly acetylcholine and tachykinins) cause rhythmic contractions of gastric smooth muscles. The gastric smooth muscles exhibit the tone on which there is superimposition of rhythmic contractions driven by cycles of membrane depolarization and repolarization.

In addition, it has been known for nearly three decades that the gastric mechanoreceptors which respond to gastric muscular distension and contraction are implicated in post-prandial satiety, in sensing the effectiveness of a contraction to expel contents, and in a variety of reflexes. Electrophysiological studies in different species have shown that mechanosensitive afferent fibers located in the antrum muscle wall respond to changes in smooth muscle transmural and local tension with an increased firing rate. Gastric distension is correlated with a firing of vagal mechanosensitive afferent fibers, which play an important role in satiety.

The physical forces that act on the intestinal wall during the intestine contraction propels chyme. The intestinal tract is abundantly innervated with mechanosensors in response to the physical forces in intestinal wall when a meal transits through the gut. The excitation of extrinsic sensory afferents provides clear evidence on the intestinal mechanosensory endings in response to distension, responding to mechanical stimulation arising during distension and contraction. The level of mesenteric afferent firing is a proportional increase when the intraintestinal pressure increases. Brain-gut interactions are recognized as major players the in physiological and pathpophysiological regulation of the intestinal tract, as the intestinal tract possesses an intrinsic nervous plexus (pacemaker) that allows the intestine to have a considerable degree of independent control from central nervous system.

Intestinal motility is one of the objectives of central nervous system and local nervous regulation. Intestinal motility disorders exist in a pathological state, such as intestinal obstruction or ileus. Laparotomy and manipulation also interfere with intestinal movements. The most widely accepted explanation of postoperative ileus was based on the idea that manipulation inhibited motor function through some sort of neurologic reflex response. Experimental studies have identified central neural influences that mediate ileus of the gastrointestinal tract. Three main mechanisms are involved in its causation, namely neurogenic, inflammatory and pharmacological mechanisms. In the acute postoperative phase, mainly spinal and supraspinal adrenergic and non-adrenergic pathways are activated. However, although the mechanical sensory and afferent excitation in response to mechanical stimulation have been extensively studied, the alteration of intestinal motility in response to mechanical stimulation is poorly understood since the response of the motility experiences a cycle of the intestinal sensor to afferent nerve to central nervous system to efferent nerve finally back to intestinal smooth muscle.

Thus, although both of the above conventional methods are widely in use, a need exists in the art for an alternative to the conventional techniques for testing vasoactivity in blood vessels such that the need addresses the setbacks and limitations of the conventional techniques, while at the same time, is easy to use and interpret and provides a more accurate measurement of vasoactivity. In addition, a need also exists in the art for various devices, systems, and methods to determine isotonic and isometric of non-vascular luminal organs, such as the stomach and the intestines.

BRIEF SUMMARY

In at least one embodiment of a method for detecting a luminal organ response to mechanical stimulation of the present disclosure, the method comprises the steps of maintaining a luminal organ at a first internal pressure, increasing the first internal pressure of the luminal organ, and measuring a first organ parameter change in response to the increase in internal pressure. In another embodiment, the luminal organ is positioned within a chamber for receiving a fluid, and wherein the fluid is in contact with the luminal organ. In yet another embodiment, the step of maintaining a luminal organ at a first internal pressure comprises the steps of positioning a conduit within an incision of the luminal organ so that a lumen of the conduit is in fluid communication with a lumen of the luminal organ, and introducing a liquid through the conduit into the lumen of the luminal organ until the luminal organ achieves the first internal pressure. In an additional embodiment, the step of increasing the first internal pressure of the luminal organ comprises the step of introducing a fluid from the conduit into the lumen of the luminal organ.

In at least one embodiment of a method for detecting a luminal organ response to mechanical stimulation of the present disclosure, the step of maintaining a luminal organ at a first internal pressure comprises the steps of positioning the luminal organ within a system for detecting a luminal organ response, introducing a fluid into a lumen of the luminal organ until a desired first internal pressure is achieved, and closing at least part of the system so that fluid is not permitted to escape the luminal organ through a component of the system. In another embodiment, the first organ parameter change is selected from the group consisting of a decrease in luminal organ diameter, an increase in luminal organ diameter, a decrease in internal luminal organ pressure, an increase in internal luminal organ pressure, and an increase in gastric contractility. In at least one embodiment, the step of measuring a first organ parameter change is performed using a device selected from the group consisting of a pressure transducer, a microscope, and a camera.

In at least one embodiment of a method for detecting a luminal organ response to mechanical stimulation of the present disclosure, the step of maintaining a luminal organ at a first internal pressure comprises the step of injecting additional fluid into a lumen of the luminal organ in response to luminal organ leakage through a wall of the luminal organ. In another embodiment, the step of injecting additional fluid is performed using a volume compensator. In another embodiment, the luminal organ is present within a living mammal.

In at least one embodiment of a system for detecting a luminal organ response to mechanical stimulation of the present disclosure, the system comprises a first conduit having a proximal end, a distal end, and a lumen therethrough, the distal end sized and shaped to fit within a luminal organ, a pressure transducer, and at least one pressurized vessel capable of introducing a fluid into the lumen of the first conduit, wherein the pressure transducer, the pressure transducer, and the at least one pressurized vessel are either directly or indirectly coupled to one another so that a pressure of a fluid present within the first conduit can be measured using the pressure transducer. In another embodiment, the system further comprises a chamber for receiving a fluid and the luminal organ. In another embodiment, the luminal organ is selected from the group consisting of a stomach, a trachea, a lymph vessel, a lymph duct, a urinary bladder, a ureter, a gall bladder, a bile duct, a hepatic duct, and an intestine. In yet another embodiment, the distal end of the conduit is positioned within an incision of the stomach so that the lumen of the first conduit is in fluid communication with a lumen of the stomach. In an additional embodiment, the distal end of the conduit is positioned within an incision of the luminal organ while the luminal organ is present within a living mammal so that the lumen of the first conduit is in fluid communication with a lumen of the luminal organ. In at least one embodiment, when the distal end of the first conduit is positioned within the luminal organ, the system is operable to detect a response of the luminal organ to an increase in internal pressure of the luminal organ.

In at least one embodiment of a system for detecting a luminal organ response to mechanical stimulation of the present disclosure, the system further comprises a chamber for receiving a fluid and the luminal organ, and wherein the chemical is introduced into the chamber. In another embodiment, the system further comprises a volume compensator in communication with the first conduit, wherein the volume compensator is operable to inject a liquid so that the liquid increases the pressure within the luminal organ. In an exemplary embodiment, the volume compensator comprises a syringe. In another embodiment, the system further comprises a device capable of detecting a physical change to the luminal organ. In yet another embodiment, the device is selected from the group consisting of a camera and a microscope. In an additional embodiment, the system farther comprises a pressure regulator in communication with the at least one pressurized vessel, the pressure regulator capable of regulating a vessel pressure.

In at least one embodiment of a method of detecting a luminal organ response to one or more chemicals of the present disclosure, the method comprises the steps of maintaining a luminal organ at a first length and a first internal pressure within a fluid bath, introducing a first chemical into the fluid bath, and measuring a first organ parameter change in response to exposure of the luminal organ to the first chemical. In at least one embodiment, the chemical causes the luminal organ to constrict. In another embodiment, the first organ parameter change is selected from the group consisting of a decrease in luminal organ diameter and an increase in internal luminal organ pressure. In yet another embodiment, the chemical causes the luminal organ to expand. In an exemplary embodiment, the first organ parameter change is selected from the group consisting of an increase in luminal organ diameter and a decrease in internal luminal organ pressure.

In at least one embodiment of a method of detecting a luminal organ response to one or more chemicals of the present disclosure, the first organ parameter change is detected using a device selected from the group consisting of a camera, a pressure transducer, and a microscope. In an exemplary embodiment, the step of maintaining a luminal organ at a first length and a first internal pressure comprises the steps of positioning the luminal organ within a system for detecting a luminal organ response, adjusting the length of the luminal organ until the first length is achieved, introducing a fluid into a lumen of the luminal organ until a desired first internal pressure is achieved, and closing at least part of the system so that fluid is not permitted to escape the luminal organ through a component of the system. In an additional embodiment, the step of maintaining a luminal organ at a first length and a first internal pressure comprises the step of injecting additional fluid into a lumen of the luminal organ in response to luminal organ leakage through a wall of the luminal organ. In another embodiment, the step of injecting additional fluid is performed using a volume compensator in fluid communication with the lumen of the luminal organ.

In at least one embodiment of a method of detecting a luminal organ response to one or more chemicals of the present disclosure, the first length is substantially a length of the luminal organ when the luminal organ was present within a mammal prior to removal of the luminal organ and placement of the luminal organ within the fluid bath. In another embodiment, the first length is longer than a length of the luminal organ when the luminal organ was present within a mammal prior to removal of the luminal organ and placement of the luminal organ within the fluid bath, and wherein the first organ parameter change is in part related to an axial overstretch of the luminal organ. In an additional embodiment, the method further comprises the steps of stretching the luminal organ to a second length, measuring a second organ parameter change in response to the exposure of the luminal organ to the first chemical, and comparing the first organ parameter change to the second organ parameter change to determine a response indicative of axial overstretch.

In at least one embodiment of a method of detecting a luminal organ response to one or more chemicals of the present disclosure, the first pressure is substantially a pressure within the luminal organ when the luminal organ was present within a mammal prior to removal of the luminal organ and placement of the luminal organ within the fluid bath. In another embodiment, the first pressure is higher than a pressure within the luminal organ when the luminal organ was present within a mammal prior to removal of the luminal organ and placement of the luminal organ within the fluid bath, and wherein the first organ parameter change is in part related to a circumferential overstretch of the luminal organ. In yet another embodiment, the method further comprises the steps of introducing a fluid into a lumen of the luminal organ so that the luminal organ has a second internal pressure higher than the first internal pressure, measuring a second organ parameter change in response to the exposure of the luminal organ to the first chemical, and comparing the first organ parameter change to the second organ parameter change to determine a response indicative circumferential overstretch.

In at least one embodiment of a method of detecting a luminal organ response to one or more chemicals of the present disclosure, the luminal organ is selected from the group consisting of a blood vessel and any mammalian organ having a lumen therein. In another embodiment, the method comprises the steps of introducing a second chemical into the fluid bath, and measuring a second organ parameter change in response to exposure of the luminal organ to the second chemical. In an exemplary embodiment, the first chemical causes an increase in intraluminal pressure and circumferential tension of the luminal organ, and wherein the second chemical causes a decrease in intraluminal pressure and circumferential tension of the luminal organ. In yet another embodiment, the method further comprises the step of determining a percent relaxation of intraluminal pressure and circumferential tension based upon at least the increase in intraluminal pressure and circumferential tension of the luminal organ in response to the first chemical and the decrease in intraluminal pressure and circumferential tension of the luminal organ in response to the second chemical.

In at least one embodiment of a system for detecting a luminal organ response to one or more chemicals of the present disclosure, the system comprises a chamber for receiving a fluid, a retaining device positioned at least partially within the chamber, the retaining device capable of retaining a luminal organ positioned therein at a first length and a first internal pressure, a first conduit coupled to the first retaining wall and a second conduit coupled to the second retaining wall, and at least one pressurized vessel, the at least one pressurized vessel coupled to at least one of the first conduit and the second conduit. In another embodiment, and when a luminal organ is retained therein, the system is operable to facilitate detection of a response of the luminal organ to one or more chemicals introduced to the luminal organ. In yet another embodiment, the chemical is introduced into the chamber. In an additional embodiment, the chemical is introduced into a lumen of the luminal organ via at least one of the first conduit and the second conduit.

In at least one embodiment of a system for detecting a luminal organ response to one or more chemicals of the present disclosure, the system further comprises a volume compensator in communication with at least one of the first conduit, the second conduit, and the at least one pressurized vessel. In another embodiment, the volume compensator is operable to inject a liquid so that the liquid increases a pressure within the luminal organ. In yet another embodiment, the volume compensator is operable to inject a liquid into the luminal organ in response to a detected loss of fluid from the luminal organ. In an additional embodiment, the volume compensator comprises a syringe.

In at least one embodiment of a system for detecting a luminal organ response to one or more chemicals of the present disclosure, the system further comprises a device capable of detecting a physical change to the luminal organ. In at least one embodiment, the device is selected from the group consisting of a camera, a pressure transducer, and a microscope. In another embodiment, the at least one pressurized vessel is operable to inject a solution present therein into the luminal organ. In yet another embodiment, the system further comprises a pressure regulator in communication with the at least one pressurized vessel, the pressure regulator capable of regulating a vessel pressure. In an additional embodiment, the retaining device comprises a first retaining wall and a second retaining wall.

DETAILED DESCRIPTION

Figure 1:
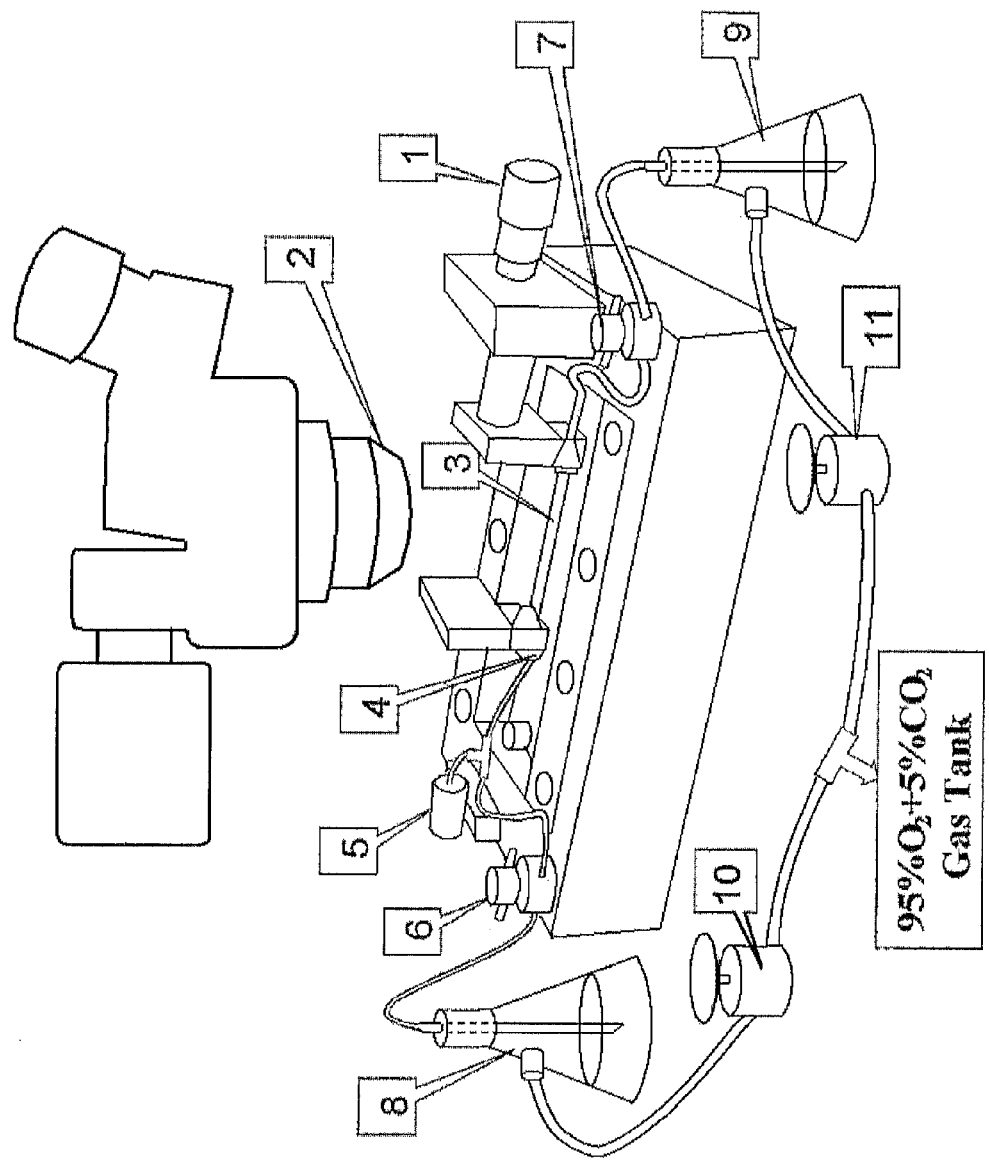
FIG. 1 shows an exemplary embodiment of an isovolumic myograph in the process of testing a blood vessel, according to the present disclosure.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

To understand and fully appreciate the advantages of the disclosure of the present application, it is useful to first consider the conventional techniques that are in use today, their uses and their drawbacks, and to consider an engineering analysis that leads to the devices, systems, and methods of the present disclosure.

Conventionally, wire and pressure myographs are widely used to study the vasoactive properties of blood vessels and other luminal organs. As referenced herein, luminal organs may include blood vessels, a stomach, and any number of other mammalian organs having a lumen therethrough. In the wire myograph, the blood vessel is cut into rings and each ring is mounted by two hooks in an isometric myograph. Typically, one of the hooks is fixed while the other is connected to a force transducer. The length of the ring is maintained relatively constant (isometric) while the measured force is recorded during vasoconstriction or vasodilatation. A useful property of this model is that it tests isometric properties with high sensitivity, but some drawbacks include the non-physiological nature of the blood vessel geometry and the mechanical loading. To remedy these drawbacks, the pressure myograph was developed.

In the pressure myograph, the blood vessel is cannulated to a perfusion system and connected to a pressurized container which can regulate the pressure. A microscope with a charge-coupled device (CCD) camera is used to monitor the diameter of the vessel. The increase or decrease of the diameter reveals the vasodilatation or vasoconstriction, respectively. In comparison with the isometric wire myograph, the measurement in the pressure myograph is more physiological.

However, the sensitivity to detect vasoactivity in the pressure myograph is lower than in the wire myograph. In other words, the force change is much larger than the diameter change in the blood vessel during vasoactivity, especially for elastic vessels. For example, the force in the isometric myograph may increase many fold during norepinephrine-induced vasoconstriction. At similar conditions, the diameter changes about 10-20% in a pressure myograph. The force in an isometric myograph may decrease to zero during acetylcholine-induced vasodilatation while the dimension changes less than 10% in a pressure myograph. Such discrepancies and variations are just some of the drawbacks of these conventional systems and must be kept in mind when considering the following engineering analysis of the reaction of blood vessels and other luminal organs in the body to determine an improved technique of measuring vasoactivity.

Under homeostatic in vivo conditions, blood vessels are arguably under more isometric than isotonic conditions. This is supported by the observation that the variation in vessel diameter is less than 10% during the cardiac cycle while the mean hoop stress ($\tau_\theta$), which can be estimated as the product of pressure (P) and inner radius ($r_i$) divided by the wall thickness (h), varies much more than that. This follows from Laplace's equation which can be stated as:

$$\tau_\theta = \frac{Pr_i}{h} \quad [1]$$

The inner radius and wall thickness are related, however, through the incompressibility principle which can be given as:

$$A_0 L_0 = \pi(r_0^2 - r_i^2)L = h(r_0 - r_i)L \quad [2a]$$

where $A_0$ and $L_0$ correspond to the wall area and length of vessel in the no-load state (zero-transmural pressure), and $r_0$ and L correspond to the outer radius and length of vessel in the loaded state. Approximating the vessel as thin walled, i.e., $r_0 \sim r_i$, Equation [2a] becomes:

$$h = \frac{A_0}{2\pi \lambda_z r_i} \quad [2b]$$

where $\lambda_z$ is the axial stretch ratio given by $L/L_0$ and $h = r_0 - r_i$. If Equations [1] and [2b] are combined, the following equation is obtained:

$$\tau_\theta = \frac{2\pi\lambda_z}{A_0} P r_i^2 \quad [3]$$

Since both pressure and radius change throughout the cardiac cycle, the change in stress will be much larger than the change in radius as shown by Equation [3]. Thus, the vessel experiences more isometric than isotonic conditions in vivo.

Furthermore, the computation of tension or stress for the cylindrical geometry using Laplace's equation requires that the vessel or other luminal organ be under equilibrium conditions. This occurs under isometric not isotonic conditions. For these reasons, the devices, systems, and methods of the present disclosure were devised to allow the determination of active mechanical properties of blood vessels and other luminal organs under isometric conditions while preserving the physiological geometry and pressure loading.

An isovolumic myograph according to the present disclosure has the advantages of both wire and pressure myographs while avoiding their limitations. In an isovolumic myograph, a blood vessel is cannulated and distended similarly to a pressure myograph, and the vasoconstriction or vasodilatation response is determined through pressure signals. Using the exemplary embodiments of the disclosure of the present application, very small pressure changes can be measured in a similar manner as the wire myograph, while maintaining a physiological geometry and loading of the blood vessel or other luminal organ similar to the pressure myograph.

Furthermore, an exemplary method of to the present disclosure is used to show that the pressure during vasoconstriction may increase up to 3-fold or higher depending on the initial pressure. Similarly, vasodilatation induces a significant pressure drop, as much as from 80 mmHg to 0 mmHg, when the vessel was pre-constricted by phenylephrine.

In an exemplary embodiment of a system of the present disclosure, an isovolumic myograph system is disclosed as shown in FIG. 1. As shown in FIG. 1, a stereomicroscope 2 is used to detect and measure the changes in dimensions and geometry of a blood vessel 3 under consideration. A micromanipulator 1 allows the length of vessel 3 to be properly positioned within the unit and connected to an axial force transducer 4. A constant and/or continuous volume is maintained through the closed unit, controllable by stopcocks 6 and 7 positioned in close proximity to either end of the blood vessel, and adjacent to flasks 8 and 9, respectively. Pressure regulators 10 and 11 are used to set and control the gas pressure within the closed fluid path which in turn controls the pressure within the lumen of vessel 3 while solid-state pressure transducer 5 detects such pressure of the fluid within the lumen of vessel 3.

Figure 5A:
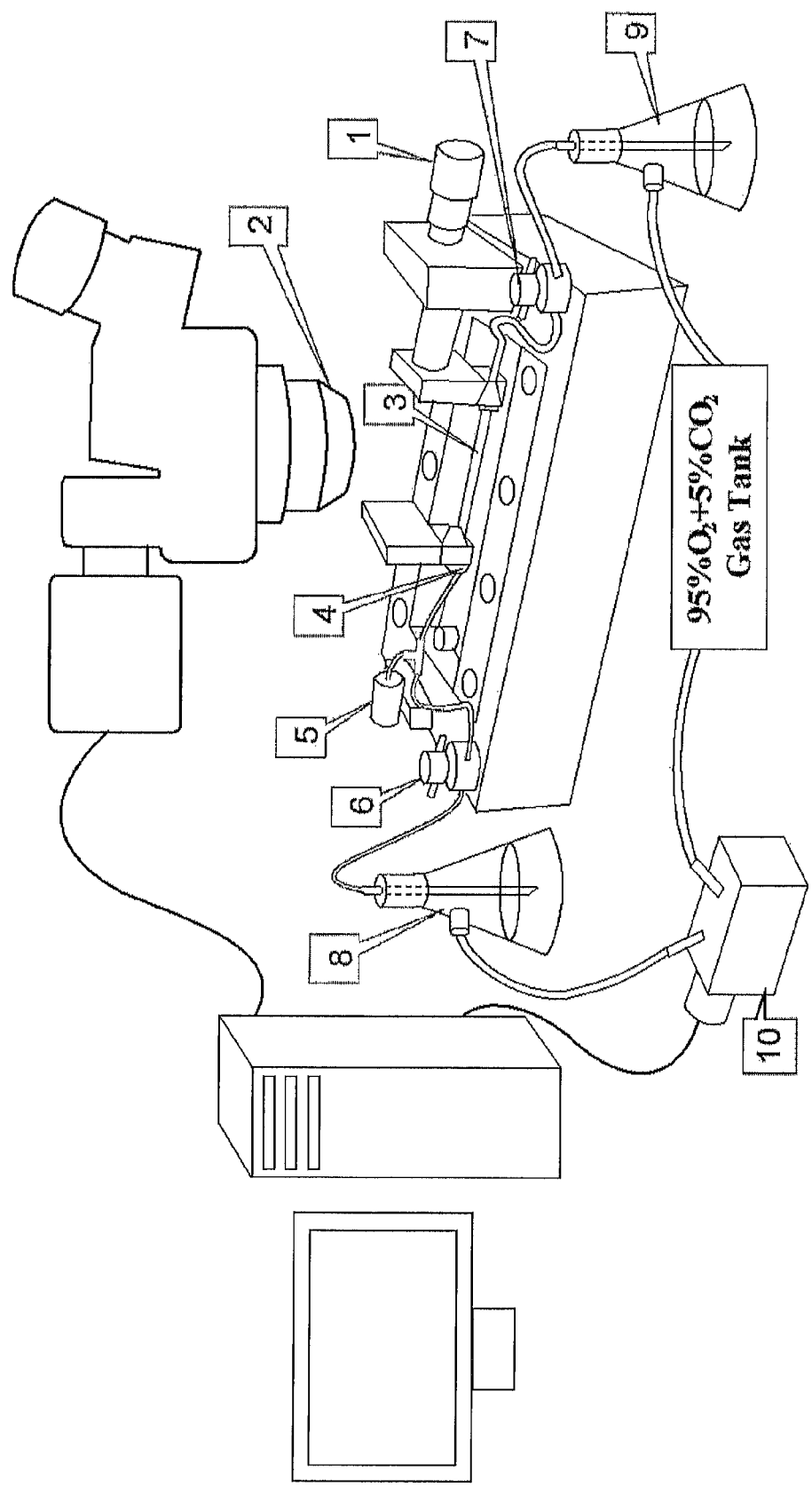
FIG. 5A shows an exemplary embodiment of an automated isometric or isotonic myograph in the process of testing a blood vessel, according to the present disclosure.

In operation, the exemplary isovolumic myograph in FIG. 1 serves to maintain an isovolumic environment for vessel 3 under consideration of and exposure to a particular drug, agonist, or the like. The various components shown in FIG. 1 serve to allow the introduction of fluid into the lumen of vessel 3, or alternatively, allow the constant flow of fluid through vessel 3. Using either method, the dimensions and stresses on vessel 3 is measured using the pressure transducer 5 and microscope 2 and recorded through a camera and recording system for later analysis. Alternatively, and as shown in FIG. 5A, a computer system may be in real-time communication with the microscope 2 and camera system such that the measurements and stresses of vessel 3 are presented in a display in real time.

To consider the measurements and analysis of the exemplary embodiment of the present disclosure as shown in FIG. 1, an experiment was conducted using arterial segments from rats. Six Wistar rats weighing 300-350 g were used in the study. The animals were anesthetized with sodium pentobarbital (60 mg/kg, ip). A heating pad was used to maintain the body temperature of the animal during anesthesia. The left carotid and common femoral arteries of the rat were exposed and cannulated for blood pressure measurements. This was done to measure the in vivo difference in blood pressure between carotid and femoral arteries. Several 1 cm segments of right carotid and femoral arteries were excised and immediately stored in 4° C. physiological saline solution (PSS).

The samples were then prepared to be tested in the exemplary isovolumic myograph according to the present disclosure as shown in FIG. 1. To prepare the samples, PSS was first contained in an organ bath with a controlled heating system and warmed to 37° C. The PSS in the organ bath was aerated by a mixture of 95% $O_2$ and 5% $CO_2$ throughout the experiment.

A micromanipulator 1 was mounted on the edge of organ bath as shown in FIG. 1. An "arm" fixed on the micromanipulator 1 was used to hold a connector to a cannulate on one end of vessel 3, and a second arm held a connector to cannulate on the other end of vessel 3. Both connectors were immersed into PSS in the organ bath and vessel 3 was cannulated on the two ends. The back ends of the two connectors were connected with thick-wall Tygon tubing to individual two-way stopcocks 6 and 7. A solid-state pressure transducer 5 was inserted into the tubing between the connector and a two-way stopcock 6 to monitor the pressure in the blood vessel 3. Each two-way stopcock 6 and 7 was connected to an individual flask (approximately 50 ml) 8 and 9, respectively, with about 20 ml of PSS (and/or another agonist) to fill the lumen of vessel 3. Each flask 8 and 9 was pressurized by a mixed 95% $O_2$ and 5% $CO_2$ gas tank, and the pressure in each flask was regulated by an independent pressure regulator 10 or 11. Regulator 10 or 11 pressurizes the fluid in the flask 8 or 9, respectively, to any desired pressure (the accuracy being to within about 1 mmHg).

Vessel 3 and pressure transducer 5 are isolated from the pressure system when vessel 3 is pressurized and the two stopcocks 6 and 7 are closed to vessel 3. Since the two ends of vessel 3 are closed off, contraction of vessel 3 causes an increase in intravascular pressure. During vasodilatation, the vessel 3 expands, and hence results in a decrease of intravascular pressure. The changes of the pressure are recorded. The diameter change, however, is very small in the isovolumic system as confirmed by a CCD camera mounted on a stereomicroscope 2 to record the diameter change. Pharmacological agonists may be endothelium-dependent, and hence could be introduced through the lumen, or may be endothelium-independent, and hence could be applied externally to vessel 3 in the bath.

With the aid of stereomicroscope 2, the adjacent loose tissue of vessel 3 was dissected carefully and all of the branches of the vessel 3 were ligated by suitable suture in 4° C. PSS. Vessel 3 was then cannulated onto the connectors in the organ bath containing PSS in room temperature and gassed by 95% $O_2$/5% $CO_2$ at 37° C. Vessel 3 was then stretched to its in vivo length and the two stopcocks 6 and 7 were opened to vessel 3. The intravascular pressure was set at 10 mmHg to allow vessel 3 to equilibrate for 40 minutes. The intravascular pressure was then increased to 60 mmHg and the two stopcocks 6 and 7 were simultaneously closed to vessel 3. Vessel 3 was challenged twice by phenylephrine at 1 μmole/L. The PSS was replaced and vessel 3 was allowed to equilibrate for 40 min. The vessel 3 segment was then pressurized to 100 mmHg in the carotid artery while the femoral artery was pressurized to 85 mmHg.

The dosage-dependent vasoconstriction in response to phenylephrine was recorded. The dosage- and endothelium-dependent vasodilatation in response to acetylcholine was also recorded in phenylephrine pre-constriction. The dosage-dependent and endothelium-independent vasodilatation in response to sodium nitroprusside (SNP) was recorded in phenylephrine pre-constriction. The maximum concentrations of agonists were then used in the pressure-dependent myogenic contraction which induced maximum vasoconstriction and vasodilation as outlined below.

Vessel 3 was then pressurized at 10 mmHg for 5 minutes and the two stopcocks 6 and 7 were closed simultaneously. The PSS with maximum concentration of phenylephrine caused vasoconstriction compared to the PSS in vessel 3. The pressure in vessel 3 and diameter of vessel 3 were recorded. The PSS with phenylephrine was drained and PSS was refilled into the organ bath. Vessel 3 was allowed to recover for 40 minutes and was then pressurized from 20 to 140 mmHg in increments of 20 mmHg. At every pressure, vasoconstriction induced by phenylephrine was repeated as outlined above. Vessel 3 was then allowed to recover for 40 minutes between every phenylephrine administration.

After the vasoactivity experiment, calcium-free PSS with 2.5 mmole/L of ethylene glycol tetraacetic acid (EGTA) was used to replace the PSS in the organ bath and flasks 8 and 9. After 20 minutes, the diameter of vessel 3 was recorded at every setting pressure: 10, 20, 40, 60, 80, 100, 120, 140, and 160 mmHg. Vessel 3 was disconnected from the organ bath and three rings (0.5 mm in length) were cut from vessel 3. The cross-section was videotaped and wall area and inner and outer perimeters were measured. The rings of vessel 3 were further cut radially and the inner and outer lengths were measured at zero-stress state.

PSS used in these experiments was made of the following (in mmole/L): 119 NaCl, 4.7 KCl, 25 $NaHCO_3$, 1.17 $KH_2PO_4$, 1.17 $MgSO_4$, 1.6 CaCl, and 5.5 glucose. Phenylephrine and acetylcholine were made in 1 mmole/L in 0.1 mmol/L HCl stock solution and stored at −20° C. The solutions were diluted and used immediately. Sodium nitroprusside was made in 1 mmole/L in PSS instantly.

Data was presented as the arithmetic mean±standard deviation (SD), unless otherwise noted. Significant differences between various parameters were determined by use of parametric analysis of variance followed by the Student t-test. A probability of $p<0.05$ was considered to be indicative of a statistically significant difference.

Figure 2:
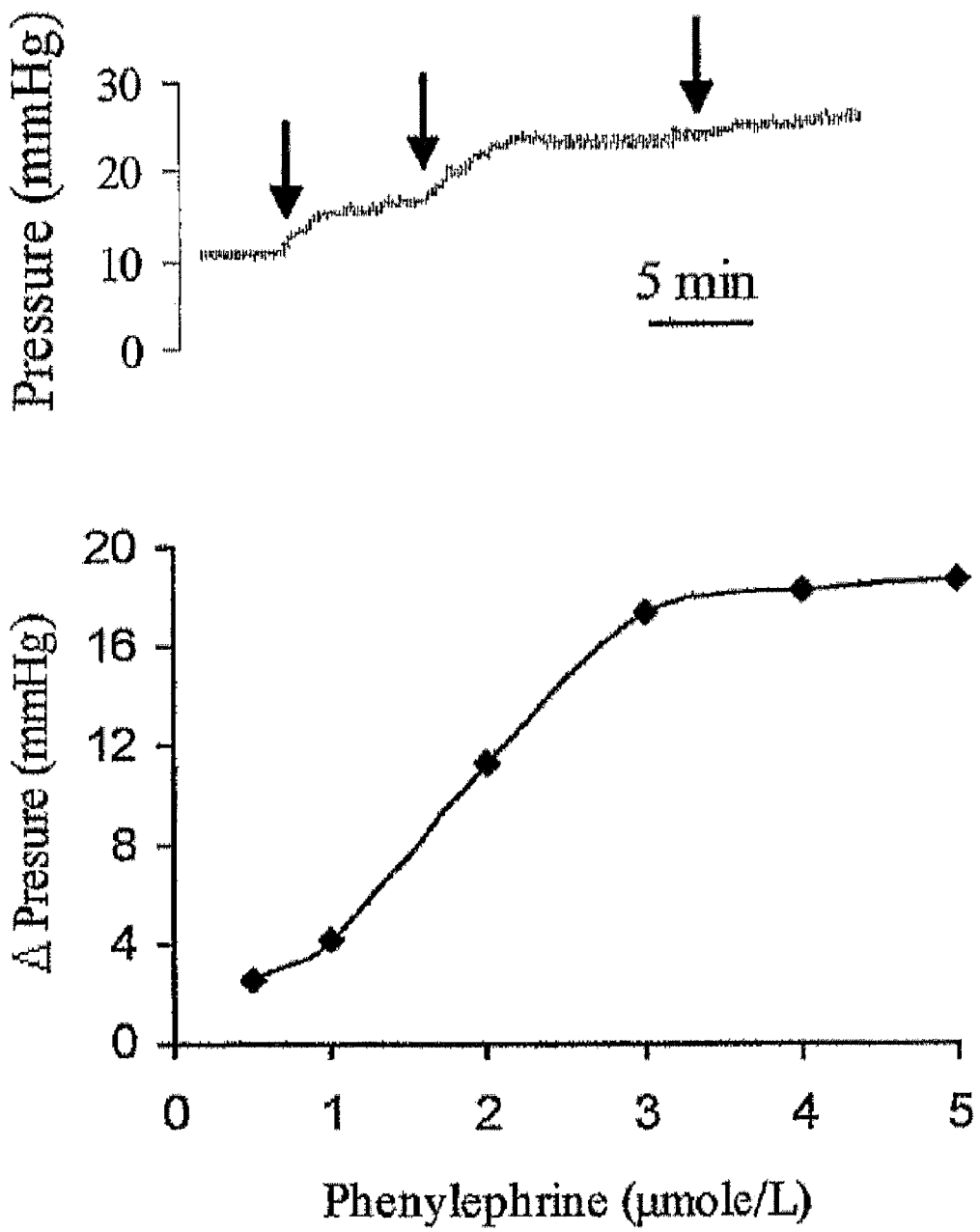
FIG. 2 shows an exemplary dosage-dependent myogenic response to phenylephrine, according to the present disclosure.

The concentration-dependent contraction of vessel 3 to phenylephrine is presented in FIG. 2. The pressure in vessel 3 increased sequentially when phenylephrine was administered in increasing concentrations, as shown by the arrow points. The pressure reached a maximum when the concentration was 3 μmole/L as shown in FIG. 2. Dosage dependent vasodilation was observed by the administration of acetylcholine.

Figure 3:
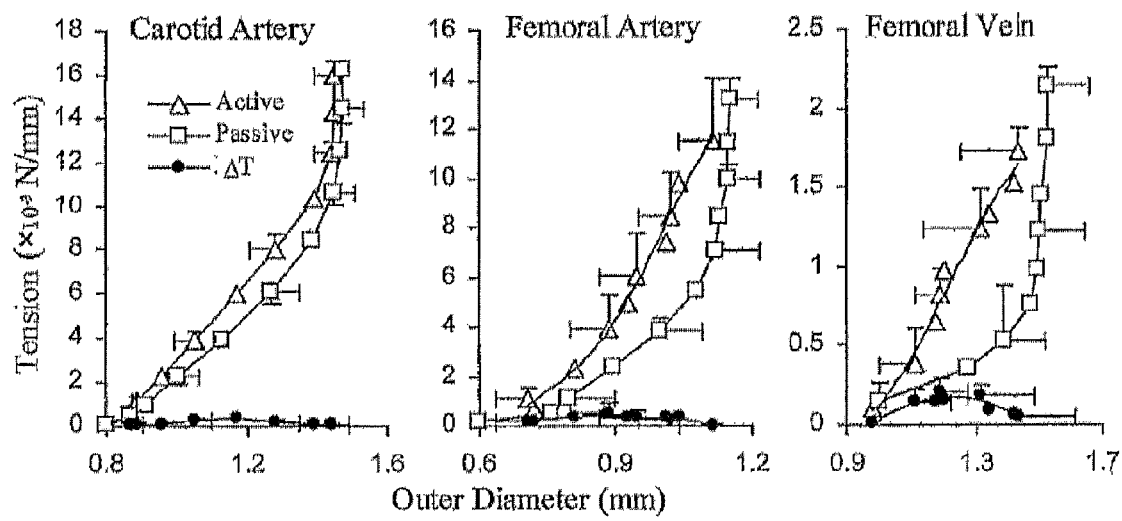
FIG. 3 shows tension-diameter relationships for passive and active properties of carotid artery and femoral artery and vein, according to the present disclosure.

FIG. 3 shows tension-diameter relationships for passive and active properties of carotid artery and femoral artery and vein. In comparison with active response to phenylephrine, the passive tension was much smaller at the same diameter. Vasoconstriction caused a large contractile force in the wall of vessel 3.

Figure 4:
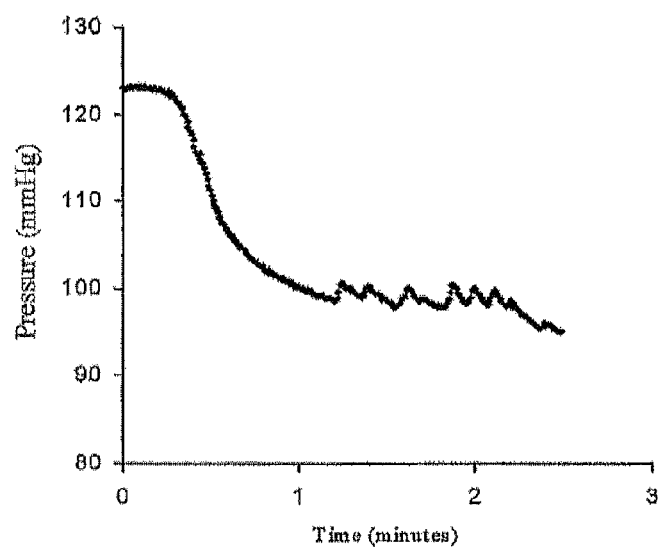
FIG. 4 shows a time course of pressure decrease during vasodilation with sodium nitroprusside (SNP), according to the present disclosure.

FIG. 4 shows a time course of pressure decrease during vasodilation with SNP. There are spontaneous small amplitude contractions during the vasodilatory process. This phenomena has not been previously reported, as it is unlikely that the diameter change is measurable with a traditional pressure myograph for these small pressure changes.

The isovolumic myograph shown in FIG. 1 is just one exemplary embodiment of a myograph of the present disclosure. Many other variations are possible and within the purview of the present disclosure. For example, the system shown in FIG. 5A is yet another exemplary embodiment of the present disclosure. This exemplary embodiment may be used for measuring isometric (FIG. 6) and isotonic (FIG. 7) vasomotion, and although it is substantially similar to the exemplary embodiment shown in FIG. 1, it also includes a computer-controlled electronic pressure or volume regulator as well as computer controlled measurement of vessel diameter.

Figure 6:
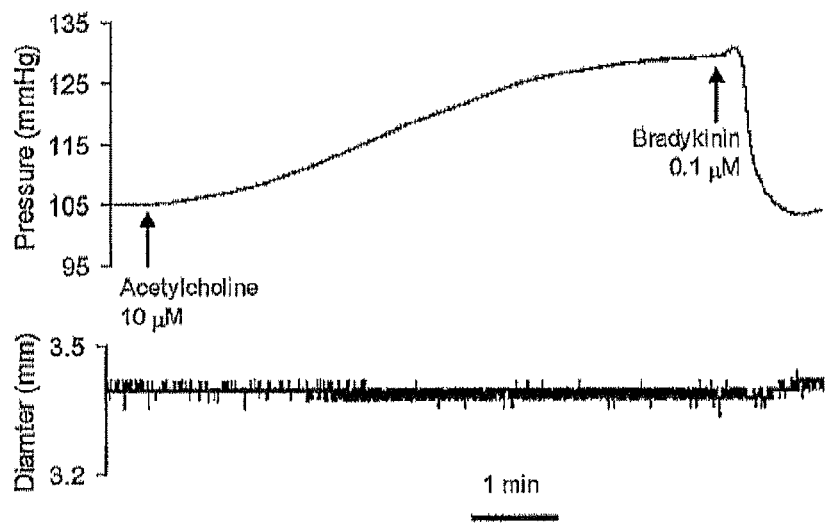
FIG. 6 shows an exemplary isometric experiment on a swine right coronary artery (RCA) reflecting a regulated pressure to maintain a constant diameter during vasomotion, according to the present disclosure.
Figure 7:
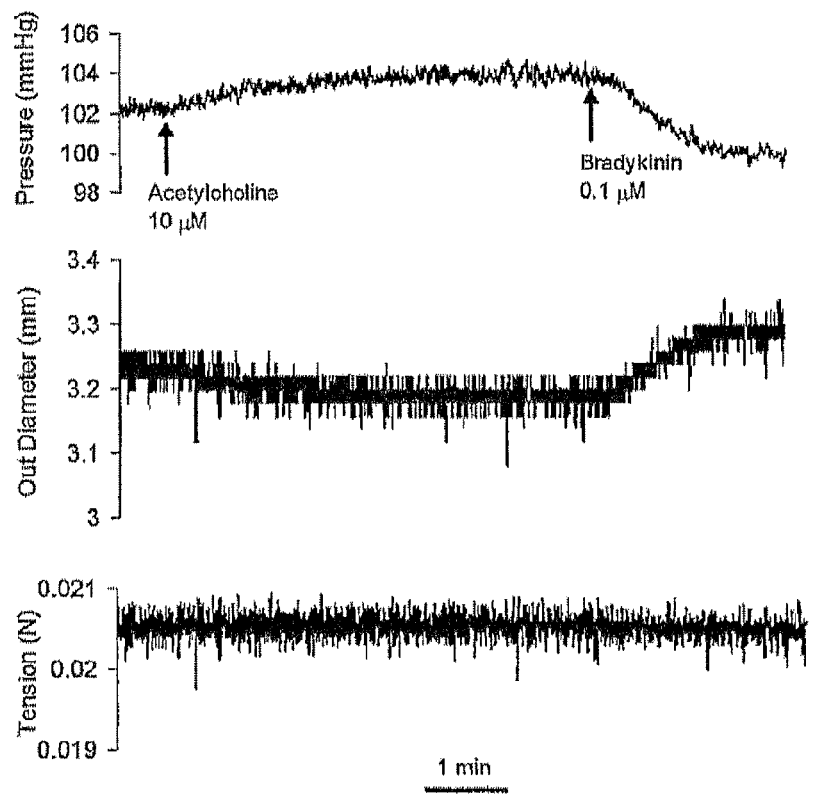
FIG. 7 shows an exemplary isotonic experiment on a swine right coronary artery (RCA) reflecting a regulated pressure to maintain a constant tension (product of pressure and diameter) during vasomotion, according to the present disclosure.

This embodiment also addresses the limitations of conventional methods, namely, that although both isometric (constant length) and isotonic (constant tension) mechanical testing have been utilized extensively in skeletal muscle preparations to understand muscle mechanics, to date, no similar device that allows both isometric and isotonic experiments in cylindrical vessels has been created, let alone with electronic and/or computer control. The isovolumic method (constant volume) can be extended to isometric and isotonic modes as well, as described with respect to FIG. 5B and as shown in FIGS. 6 and 7, respectively.

Figure 5B:
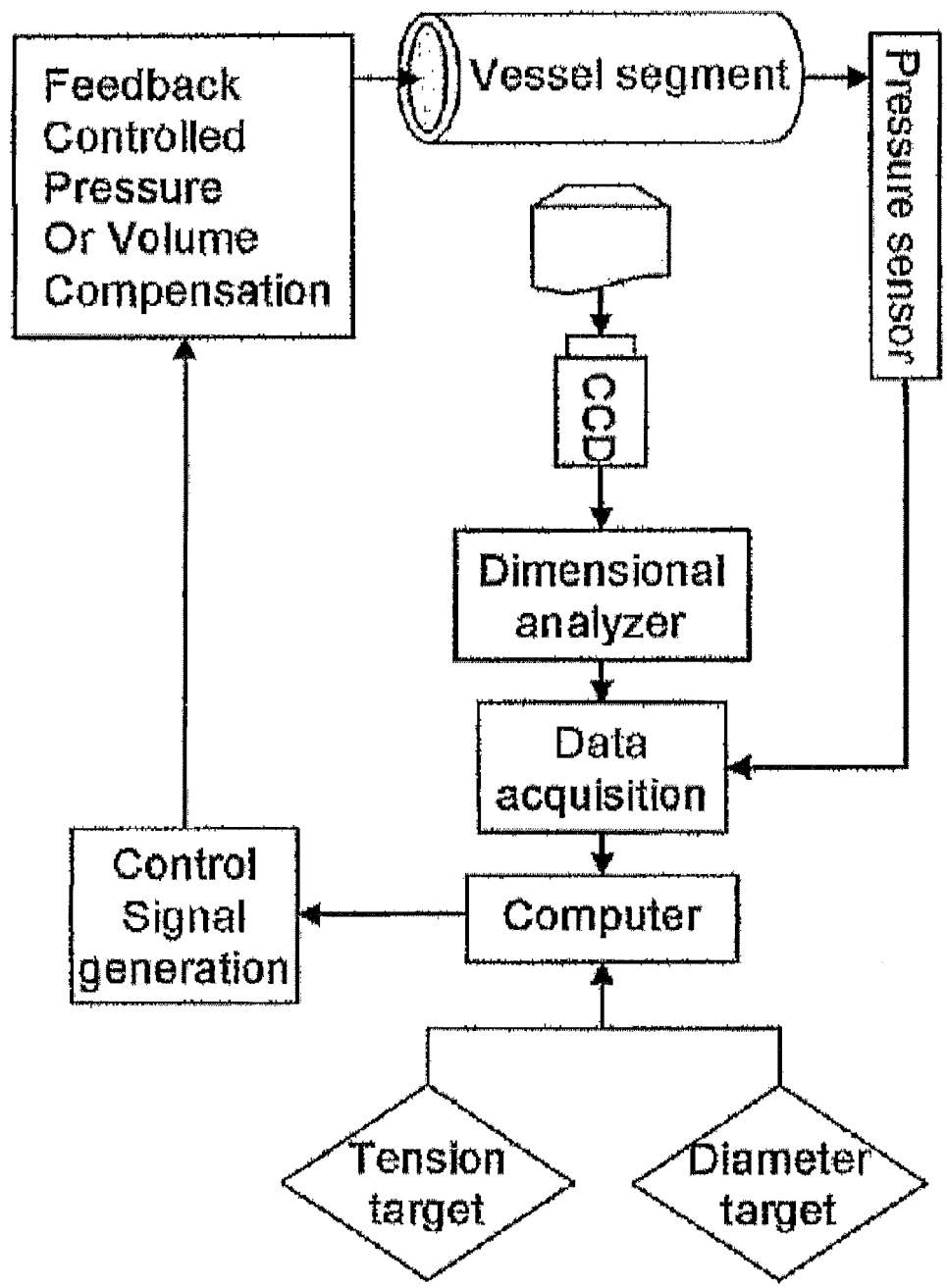
FIG. 5B shows a pressure or volume control feedback loop as used in one or more exemplary embodiments of the present disclosure.

FIG. 5B shows a schematic feedback loop for the isometric and isotonic measurements used in the exemplary embodiment of FIG. 5A. To better understand the feedback loop control of this embodiment, first, isometric vasoactivity is considered. The diameter of vessel 3 will increase or decrease during relaxation or contraction, respectively. The isometric vasomotion requires that vessel 3 diameter during vasoactivity is maintained constant by regulating the pressure or volume. Therefore, pressure or volume is regulated in a feedback loop to a set diameter. During vasoconstriction, the reference diameter is decreased. The system measures the decrease in diameter and responds by increasing the pressure or volume to the set value. The feedback loop is reiterated until the diameter is maintained within 1% of the set value. Conversely, pressure or volume is decreased during vasodilatation to decrease the diameter to the set value through a negative feedback loop as shown in FIG. 6.

Next, isotonic vasoactivity is considered. Isotonic vasomotion requires that circumferential tension of vessel 3 be constant (e.g., the product of pressure and inner radius is constant). During isotonic contraction, the circumferential tension is maintained constant but both pressure and diameter change as shown in FIG. 7. Briefly, the set point is computed as the product of pressure and diameter and the system will vary the pressure or volume to maintain a constant product similar to the isometric test.

In performing isometric and isotonic tests, the vessel diameter is measured. Typically, the smaller diameter of the vessel, the more transparent it is. Hence, the inner and outer diameters can be measured directly in smaller vessels. In the present system, the inner diameter can be continuously measured very well for vessels<600 μm in diameter. For vessels>600 μm in diameter, only the outer diameter can be measured directly. The inner diameter can be calculated from methods established in the art based on measurements of no-load cross-sectional area, axial stretch ratio and the incompressibility assumption. Hence, the inner diameter may be computed from the outer diameter and additional measurements as described above.

Figure 8:
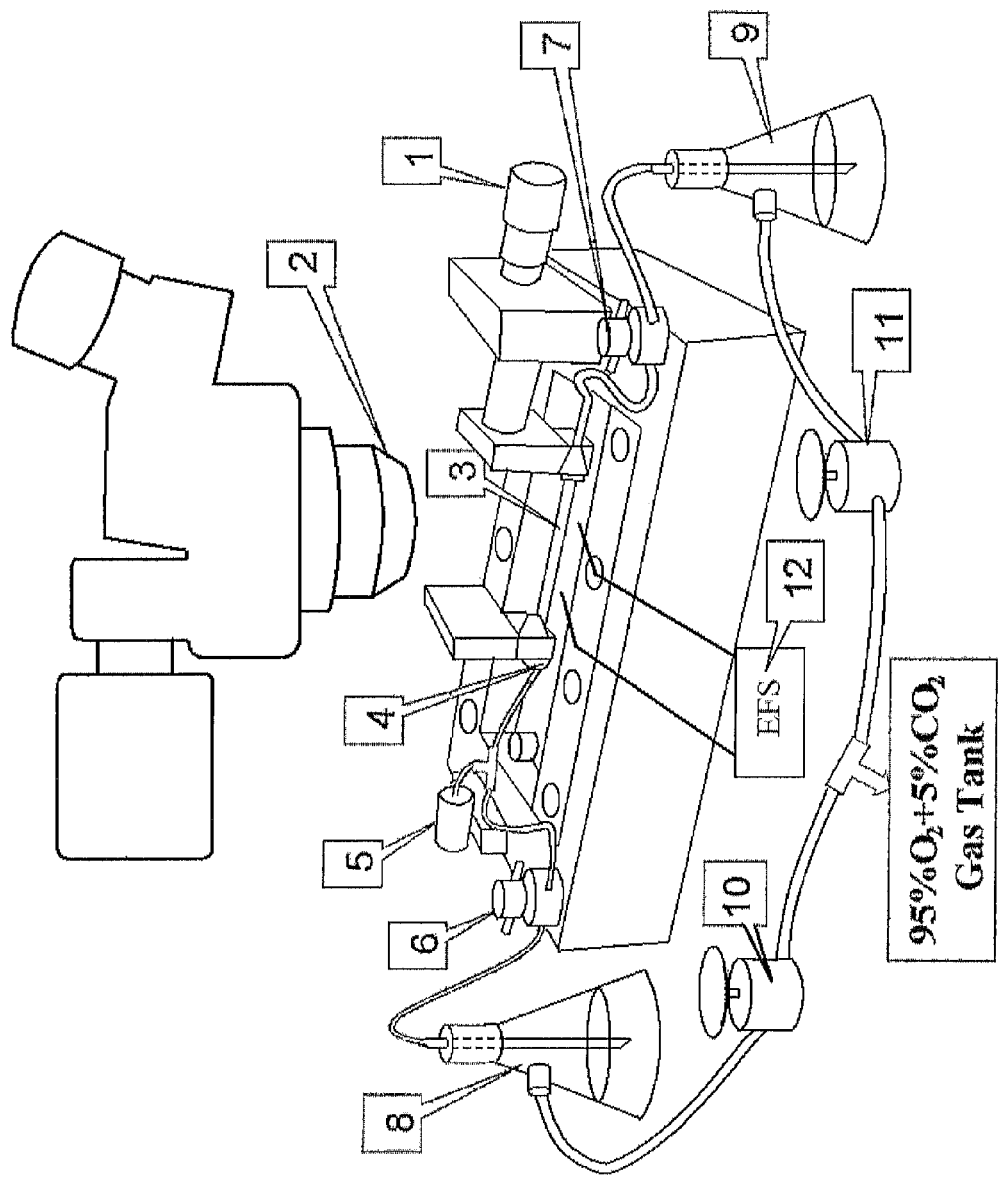
FIG. 8 shows an exemplary embodiment of an isovolumic myograph having electrical stimulus and in the process of testing a blood vessel, according to the present disclosure.

As discussed above, there are several modes of vessel smooth muscle activation, including, for example: (1) physical, such as increase in pressure during myogenic response; (2) chemical, such as with various agonist and antagonist through pharmacological agents; and (3) electrical, through current stimulation. The first two are referenced generally within the present disclosure, and the third type is discussed with respect to FIG. 8, which shows an arrangement where an electrical current source 12 can be used to stimulate the contraction of vessel by electrical field stimulation (EFS). A variety of electrodes may be used to provide such a stimulus. As a non-limiting example, two platinum wire electrodes may be used to stimulate the vessel segment with an electronic stimulator by 20 Hz with square wave pulses of 0.3-ms duration and 60 mV. This embodiment can be used to show various vasoactivity in response to electrical stimulation.

Figure 9:
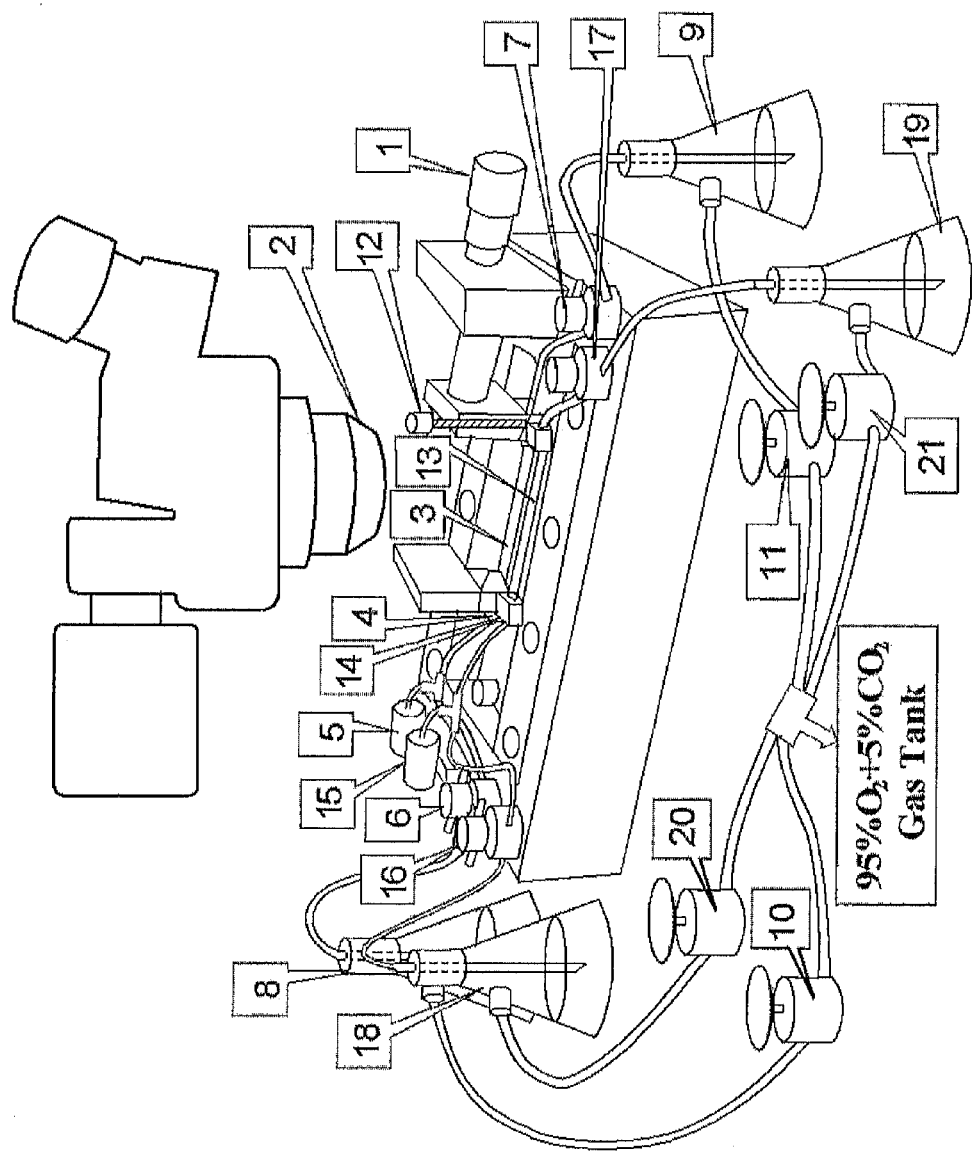
FIG. 9 shows an exemplary embodiment of an isovolumic multi-vessel myograph, according to the present disclosure.

FIG. 9 shows yet another exemplary embodiment according to the present disclosure wherein multiple vessels may be tested in the same system. In this particular example, a second vessel 13 may be simultaneously measured in the same organ bath as the first blood vessel 3. The tubing, force transducer 14 and pressure transducer 15, stopcocks 16 and 17, flasks 18 and 19, and fine pressure regulators 20 and 21 are similar to those used for the first vessel 3, and as described in the aforementioned exemplary embodiments. An additional manipulator 12 may be used to adjust the length of second vessel 13 length independently of the first vessel 3. The second vessel 13 may be exposed to the same vasostimulators or pressure loading as the first vessel 3. Using such a system, different vessels from different parts of the body may be tested for response to same or similar stimuli. Other uses are also possible, as referenced below.

Figure 10A:
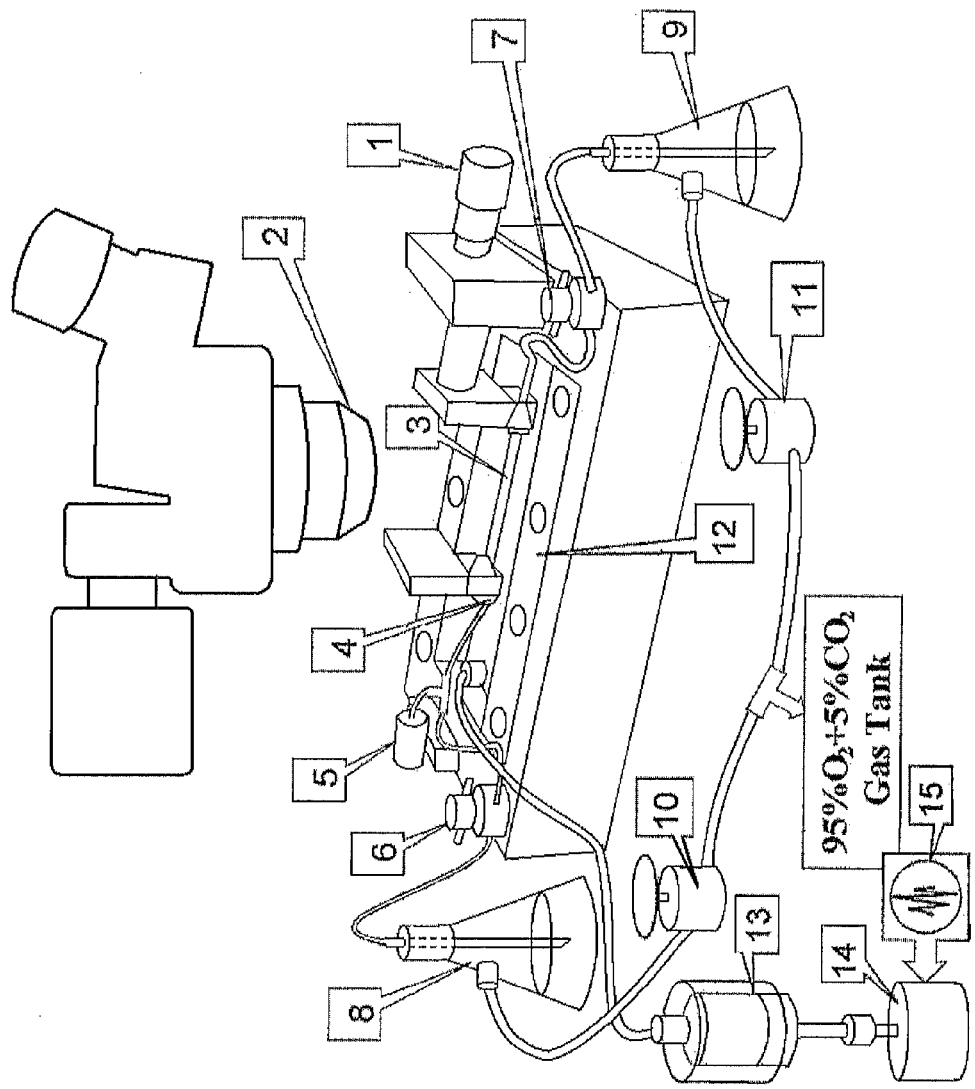
FIG. 10A shows an exemplary embodiment of an isovolumic multi-pressure myograph, according to the present disclosure.

In yet another exemplary embodiment, as shown in FIG. 10A, a system is provided that allows the testing of a vessel wherein the internal and external pressures of a vessel may be controlled. Further, a particular pulse pressure 15 may be electronically produced by pulse pressure generator 14 and forwarded to pressure transducer 13, leading to sealed external bath 12 containing vessel 3. Sealed external bath 12 is secured such that the external pressure of the vessel 3 is controllable by the pressure pulse system. Such an exemplary system allows an even more realistic model of the actual vessel environment that may be used to test a vessel as it experienced pulsatile pressure changes. Other tests and configurations are possible and are within the scope of the present disclosure.

Figure 10B:
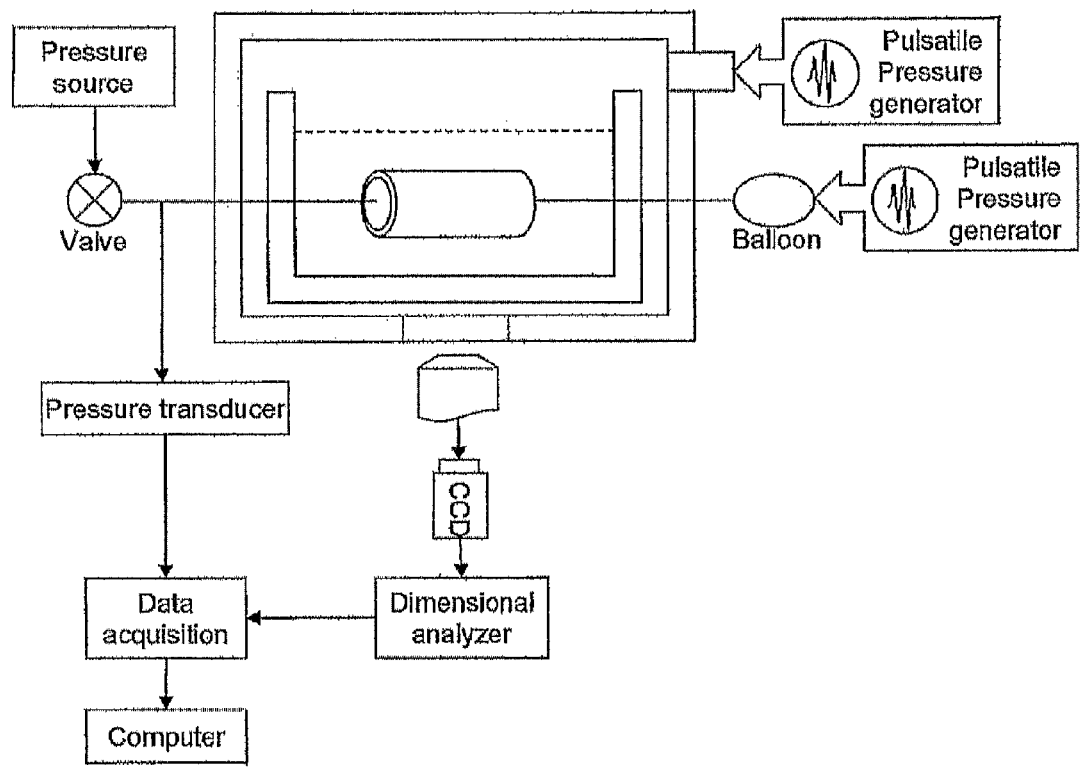
FIG. 10B shows a schematic perspective of an exemplary myograph having multiple pulsatile pressure controls, according to the present disclosure.

In vivo, vessels experience pulsatile intravascular pressure conditions. Furthermore, some vasculatures, such as the coronary vessels, experience pulsatile external loading in addition to pulsatile intravascular loading. Hence, it is very useful to mimic both intravascular as well as external pulsatile loading conditions shown in an exemplary embodiment of the present disclosure as referenced in FIG. 10B. This exemplary embodiment shows a schematic of an isovolumic system that enables internal and external pulsatile pressure conditions. This can be readily done using the disclosure of the present application by pressurizing the external medium (solution bath) of the vessel with a pulsatile pressure apparatus. To generate internal pulsatile pressures, a compliant balloon is connected in series with the vessel. The balloon is then loaded externally with a pulsatile pressure. The pressure pulse is transmitted to the lumen of the vessel through the compliant balloon.

Although the above examples show some of the advantages of the present disclosure, additional benefits and abilities are also inherent and apparent herein. For example, a myogenic response may be measured through a pressure response after a sudden change in pressure. In addition, axial force measurements may be made allowing for measurement of simultaneous axial forces.

Yet another advantage of the present disclosure is that the filtration rate in small vessels may also be determined, wherein the filtration rate can be computed during an isovolumic experiment. Consider a vessel of cylindrical geometry whose volume is given by $$V = \frac{\pi}{4} D^2 L \quad [4]$$

A change in volume during an isovolumic contraction is due to filtration and can be related to the diameter change as follows:

$$\delta V = \frac{\pi}{2} D L \delta D \quad [5]$$

The filtration rate, $J_V$, can be given as $$J_V = \frac{\delta V}{\delta t} = \frac{\pi}{2} D L \frac{\delta D}{\delta t} \quad [6]$$

The filtration rate per surface area, S, can be expressed as $$J_V / S = \frac{1}{2} \frac{\delta V}{\delta t} \quad [7]$$

Hence, the filtration rate is equal to one half of the rate of change of diameter which can be quantified during the experiment.

In addition to the foregoing, the disclosure of the present application includes a method through an on-line real-time measurement of pressure which can be extended to the full range of vessels (arterioles to aorta) using the various systems referenced herein. Such methods demonstrate that the physiologic loading (circumferential and axial) significantly affects endothelial function and hence the preservation of physiological geometry and loading conditions are essential for a functional endothelial assay.

Animals and tissue preparation. To demonstrate the foregoing, Wistar male rats were obtained at 3 months of age (from Charles River, Wilmington, Mass., USA). Six aorta, six femoral arteries, and six mesenteric arteries were harvested from eighteen rats. The animals were acclimated to the testing facility for approximately one week prior to the start of the study. On the day of termination, each animal was first anesthetized with sodium pentobarbital (80 mg/kg, i.p.) and euthanized by overanesthesia with sodium pentobarbital (300 ng/kg, i.p.). Either the aorta, common femoral artery, or mesenteric artery were excised quickly and placed in ice-cold physiological saline solution (PSS in mmole/L: 119 NaCl, 4.7 KCl, 25 NaHCO$_3$, 1.17 KH$_2$PO$_4$, 1.17 MgSO$_4$, 1.6 CaCl, 5.5 Dextrose, solution gassed by 95% O$_2$/5% CO$_2$). The artery was carefully cleaned from adjacent tissue with the aid of a stereo-dissection microscope. The branches on the artery were ligated and the artery was allowed to warm up to room temperature (22° C.) slowly in approximately 10-15 min. The artery was transferred to the chamber of isovolumic system and cannulated with connectors and secured with 8-0 suture twice to avoid any leakage. The artery was warmed up to 37° C. slowly (20-25 min) and equilibrated for 40 min at a transmural pressure of 15 mmHg before agonist and antagonist stimulation.

Figure 11A:
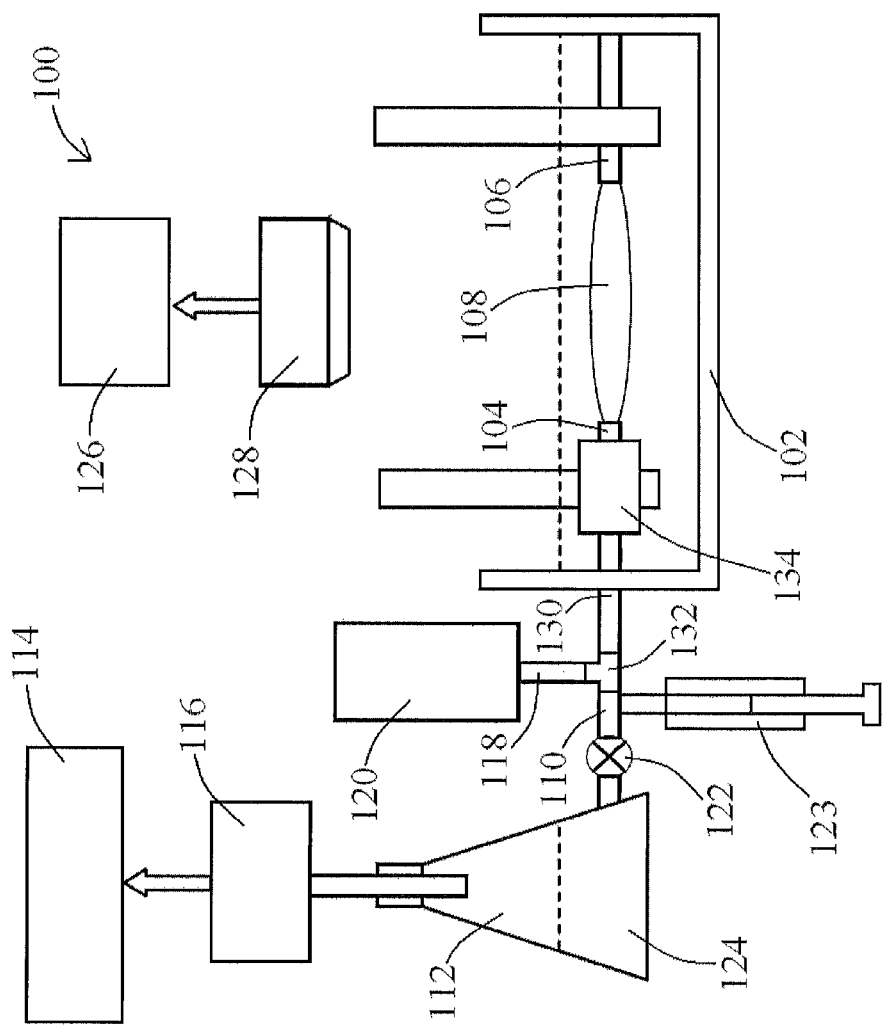
FIGS. 11A and 11B show exemplary embodiments of an isovolumic myographs, according to the present disclosure.

Isovolumic myography. An isovolumic myograph system, such as shown in FIG. 11A, was used in the present study. As referenced herein, such an isovolumic myograph system 100 comprises a chamber 102 for receiving a fluid, and two connectors 104, 106 (exemplary retaining devices) which bridge the bodily vessel 108 and various tubes of system 100. One tube 110, as shown in the exemplary system 100 shown in FIG. 11A, connects to a pressurized vessel 112 (such as a 50 mL flask with PSS therein, for example), whereby vessel 112 is pressurized with gas source 114 and a regulator 116 to inflate/pressurize vessel 112 at the desired pressure. Another tube 118 connects to a solid state pressure transducer 120 to monitor the transmural pressure. A volume compensator 123 (a syringe, for example), may also be coupled to a tube of system 100 to compensate for water transport across the wall of vessel 108. The outlet of tube 110, for example, may be blocked to achieve isovolumic conditions by way of stopcock 122 coupled thereto.

PSS (an exemplary fluid 124) fills the various tubes prior to vessel 108 cannulation. A CCD camera 126 mounted on a stereomicroscope 128, for example, may be used to transfers image(s) of vessel 108 to a computer (as shown in FIG. 5A, for example), that digitizes the external diameter of vessel 108. Since the sample rate of digital conversion (200/sec in at least one embodiment) is higher than the rate of change in vessel 108 during vasoreactivity, the diameter is easily tracked using such components.

To start the study, vessel 108 is inflated to a desired pressure; e.g., physiologic pressure. Since the outlet is closed off, there is no flow of fluid in vessel 108 and vessel 108 is merely pressurized. To achieve isovolumic state, a clamp (not shown) placed on a tube between the vessel 112 and connector 104, and/or stopcock 122 is used, for example, to close the system 100 and to seal the PSS in the lumen of the vessel and tubes; i.e., volume is constant. The vascular contraction or relaxation during chemical stimulation is characterized with significant changes of intraluminal pressure.

Figure 11B:
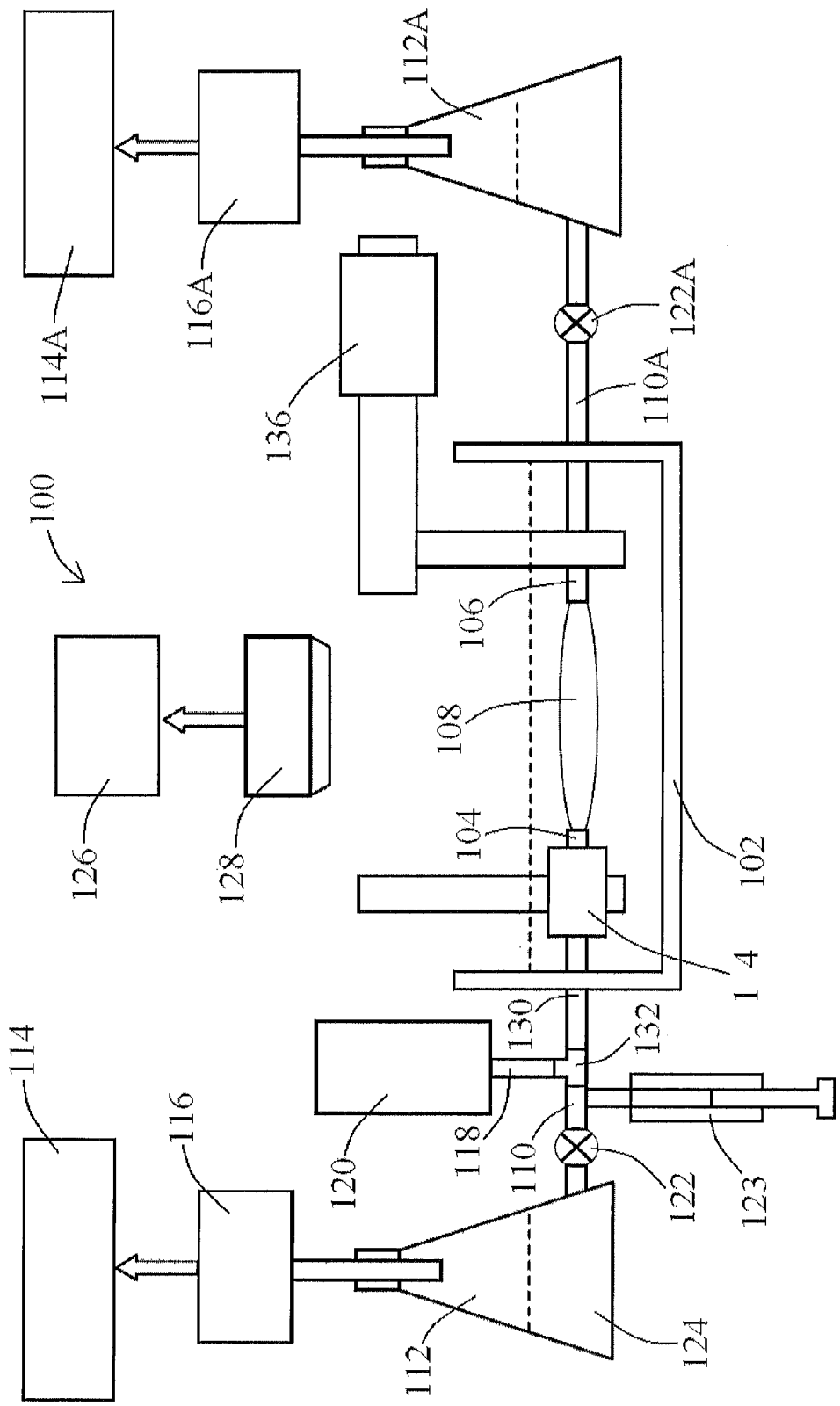

In addition to the foregoing, various other components of systems 100 and 200 (referenced below) as disclosed herein may be part of such an exemplary system 100. For example, an additional tube 130 may be coupled to system 100 between connector 104 and connector 132 so that tubes 110, 118, and 130 may couple to and be in fluid communication with one another as shown in FIG. 11A. In addition, and as shown in FIG. 11A, system 100 may comprise an axial force transducer 134 to facilitate adjustment of a vessel present within system 100. Furthermore, and as shown in the exemplary system 100 of the present disclosure shown in FIG. 11B, system 100 may further comprise a micromanipulator 136 to permit a user to manipulate the length of vessel 108. In addition, an exemplary system 100 may comprise a second tube 110A, a second stopcock 122A, a second vessel 112A, a second pressure regulator 116A, and a second gas source 114A, as shown in FIG. 11B. Gas sources 114 and 114A may comprise the same gas source, whereby the same gas source is in communication with pressure regulators 116 and 116A.

Figure 11C:
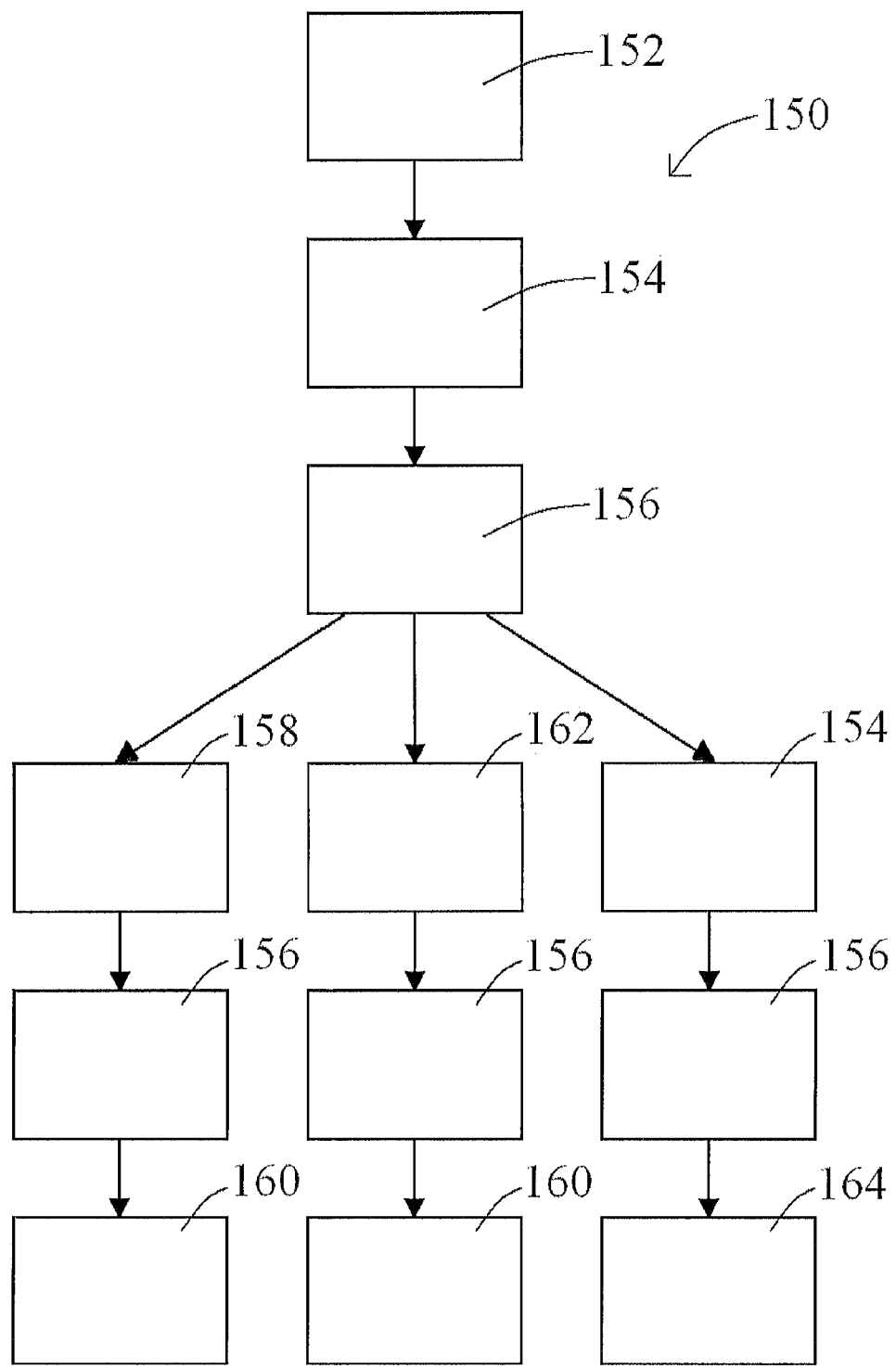
FIG. 11C shows steps of an exemplary method of detecting a luminal organ response to one or more chemicals, according to the present disclosure.

Steps of an exemplary method of detecting a luminal organ response to one or more chemicals of the present disclosure is shown in FIG. 11C. As shown in FIG. 11C, an exemplary method 150 comprises the steps of maintaining a luminal organ at a first length and a first internal pressure within a fluid bath (an exemplary maintenance step 152), introducing a first chemical into the fluid bath (an exemplary chemical introduction step 154), and measuring a first organ parameter change in response to exposure of the luminal organ to the first chemical (an exemplary parameter change measurement step 156). In at least one embodiment, and if the chemical causes the luminal organ to constrict, the first organ parameter change may be a decrease in luminal organ diameter and/or an increase in internal luminal organ pressure. In another embodiment, and if the chemical causes the luminal organ to expand, the first organ parameter change may be an increase in luminal organ diameter and/or a decrease in internal luminal organ pressure. Such changes may be detected using a camera, a pressure transducer, and/or a microscope, for example, but are not limited to those exemplary detection devices.

In at least one embodiment of an exemplary method 150 of the present disclosure, maintenance step 152 comprises positioning the luminal organ within a system for detecting a luminal organ response, adjusting the length of the luminal organ until the first length is achieved, introducing a fluid into a lumen of the luminal organ until a desired first internal pressure is achieved, and closing at least part of the system so that fluid is not permitted to escape the luminal organ through a component of the system. In addition, maintenance step 152 may also comprise injecting additional fluid into a lumen of the luminal organ in response to luminal organ leakage through a wall of the luminal organ. Such an injection may be performed using a volume compensator in fluid communication with the lumen of the luminal organ.

As referenced in further detail herein, the luminal organ may be overstretched or inflated when performing an exemplary method 150. In at least one embodiment, the first length is substantially a length of the luminal organ when the luminal organ was present within a mammal prior to removal of the luminal organ and placement of the luminal organ within the fluid bath. In another exemplary embodiment, the first length is longer than a length of the luminal organ when the luminal organ was present within a mammal prior to removal of the luminal organ and placement of the luminal organ within the fluid bath, and wherein the first organ parameter change is in part related to an axial overstretch of the luminal organ.

An exemplary method 150 of the present disclosure, as shown in FIG. 11C, may further comprise the steps of stretching the luminal organ to a second length (an exemplary stretching step 158), measuring a second organ parameter change in response to the exposure of the luminal organ to the first chemical (also an exemplary parameter change measurement step 156), and comparing the first organ parameter change to the second organ parameter change to determine a response indicative of axial overstretch (an exemplary comparison step 160).

In an exemplary embodiment of a method 150 of the present disclosure, the first pressure is substantially a pressure within the luminal organ when the luminal organ was present within a mammal prior to removal of the luminal organ and placement of the luminal organ within the fluid bath. In another embodiment, the first pressure is higher than a pressure within the luminal organ when the luminal organ was present within a mammal prior to removal of the luminal organ and placement of the luminal organ within the fluid bath, and wherein the first organ parameter change is in part related to a circumferential overstretch of the luminal organ.

Another exemplary method 150 of the present disclosure, as shown in FIG. 11C, may further comprise the steps of introducing a fluid into a lumen of the luminal organ so that the luminal organ has a second internal pressure higher than the first internal pressure (an exemplary fluid introduction step 162), measuring a second organ parameter change in response to the exposure of the luminal organ to the first chemical (also an exemplary parameter change measurement step 156), and comparing the first organ parameter change to the second organ parameter change to determine a response indicative circumferential overstretch (also an exemplary comparison step 160). In at least one embodiment of a method 150 of the present disclosure, method 150 may further comprise the steps of introducing a second chemical into the fluid bath (also an exemplary chemical introduction step 154), and measuring a second organ parameter change in response to exposure of the luminal organ to the second chemical (also an exemplary parameter change measurement step 156) as shown in FIG. 11C.

In various embodiments of methods 150 and 250 (as referenced in detail herein), the luminal organ is selected from the group consisting of a blood vessel and any mammalian organ having a lumen therein. In at least one embodiment, the first chemical causes an increase in intraluminal pressure and circumferential tension of the luminal organ, and wherein the second chemical causes a decrease in intraluminal pressure and circumferential tension of the luminal organ. In such an embodiment, and as shown in FIG. 11C, method 150 may further comprise the step of determining a percent relaxation of intraluminal pressure and circumferential tension based upon at least the increase in intraluminal pressure and circumferential tension of the luminal organ in response to the first chemical and the decrease in intraluminal pressure and circumferential tension of the luminal organ in response to the second chemical (an exemplary percent relaxation step 164).

Volume compensation due to fluid filteration: Although the various systems and methods of the present disclosure can achieve a fairly constant volume of the solution in the lumen of a vessel, it is not strictly constant since the PSS may be transported across the vessel wall (water flux) driven by the transmural pressure. Although the rate of water flux is very small (<1 nl/min) and no visible reduction of diameter is seen during the duration of experiment (<1 hr.), a pressure drop, namely a drop in baseline pressure, is observable. In order to stabilize the baseline of pressure, a volume compensator may be connected in parallel with pressure transducer. The volume compensator comprises a gastight connector, a microsyringe (maximum volume: 25 µl), a microsyringe pump (UltraMicroPump III, World Precision Instruments, USA) and a microsyringe pump controller (Micro 4™, World Precision Instruments, USA). The criteria for compensatory rate of microsyringe pump controller is to maintain the transmural pressure at the desired baseline value. There is no measurable change of vessel diameter during compensation. If the leak rate was >1 µl/min, the specimen was discarded as the vessel wall was damaged.

Tension and percent relaxation: The circumferential tension can be computed based on the following:

$$T = \frac{P \times r_{int}}{2} \quad [8A]$$

and $$r_{int} = \sqrt{r_{ext}^2 - \frac{A_0}{\pi \lambda}} \quad [8B]$$

wherein T is circumferential tension given by Laplace's equation (Equation [8A], P is intraluminal pressure, and $r_{int}$ is internal radius of blood vessel related to the external radius, through the incompressibility assumption (Equation [8B]). $A_0$ is the cross-sectional wall area of vessel at no-load state (zero intraluminal pressure), and $\lambda$ is axial stretch ratio.

Figure 12:
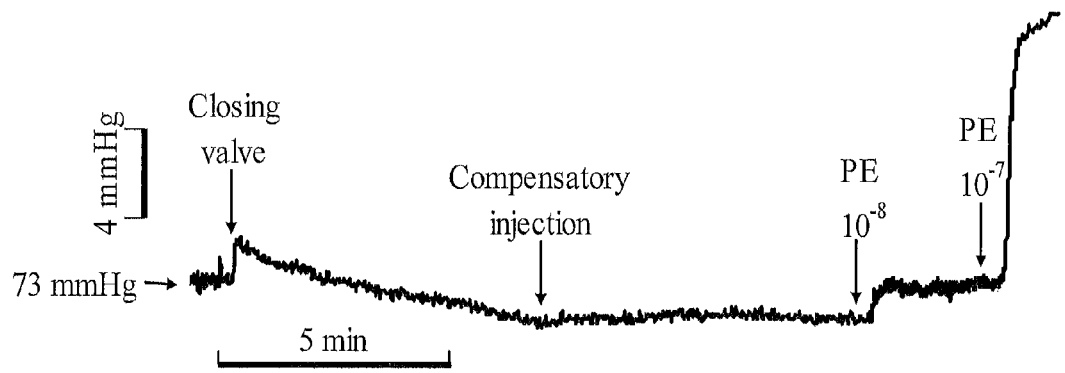
FIG. 12 shows a typical tracing curve of intraluminal pressure before and after volume compensation, and thereafter in response to vasoconstriction, according to the present disclosure.

A dose-dependent vasoconstriction and vasodilatation in response to phenylephrine (PE) and acetylcholine (ACh) were carried out under isovolumic conditions. Briefly, the artery was stimulated to contract with phenylephrine (PE) that was injected the PSS in the chamber to increase PE concentration of the PSS step by step from $10^{-10}, 10^{-9}, \ldots,$ to $10^{-5}$ mole/l, as shown in FIG. 12. FIG. 12 shows a typical tracing curve of intraluminal pressure before and after volume compensation, and thereafter in response to vasoconstriction. The vessel segment was femoral artery which was stretched to its in vivo length and inflated to ~70 mmHg, and closed the valve and compensated, and then stimulated with PE (phenylephrine, mole/L). The compensatory rate was 38 nl/min. Then, the artery was relaxed with acetylcholine (ACh) by a series of doses: $10^{-10}, 10^{-9}, \ldots, 10^{-5}$ mole/l in the PSS. The relaxation results in the reductions of intraluminal pressure and circumferential tensions which was computed using Equations [8A] and [8B]. The calculation of percent relaxation (% R) was based to both intraluminal pressure (% $R_P$) and tension (% $R_T$) for comparsion:

$$\% R_P = (P_d - P_i)/(P_{max} - P_i) \times 100 \quad [9A]$$

and $$\% R_T = (T_d - T_i)/(T_{max} - T_i) \times 100 \quad [9B]$$

wherein $P_d$, $P_i$, and $P_{max}$ are the intraluminal pressures at each dose ($P_d$), inflation pressure ($P_i$), and maximum pressure ($P_{max}$) at 0 mole/l of ACh, respectively. $T_d$, $T_i$, and $T_{max}$ are the circumferential tension at every dose ($T_d$), physiological level ($T_i$), and maximum tension ($T_{max}$) at 0 mole/l of ACh, respectively.

Effects of over-stretch on endothelial function of femoral artery. The loading perturbation was only superimposed on the femoral artery. After the test of endothelium-dependent relaxation, the femoral artery was incubated in fresh PSS for 90 minutes to restore endothelial function. The femoral artery was, then, exposed to mechanical perturbation with either axial over-elongation (stretch ratio of 1.47 from 1.3, 118% increase) or over-inflation (pressure of 120 from 70 mmHg, 170% increase). The stretch ratio of 1.3 is the length ratio of in vivo to ex vivo since the excised vessel shrinks approximate 30%. In axial over-stretch, the vessel was stretched to ratio 1.47 and inflated to physiologic pressure 70 mmHg. The vasoreactivity was performed according to the above protocol. In over-inflation, the vessel was inflated to 120 mmHg and stretched to physiologic stretch ratio of 1.3. Sodium nitroprusside (SNP)-induced vasorelaxation was applied to evaluate the endothelium-independent vasorelaxation.

Data Analysis and Statistics: The relation of the % Relaxation between tension (% $R_T$) and transluminal pressure (% $R_P$) measurements were expressed by % $R_P = \alpha$ % $R_T + \beta$, where $\alpha$ and $\beta$ are empirical constants that were determined with a linear least squares fit and a corresponding correlation coefficient $R^2$. In a Bland-Altman scatter diagram, the percent differences between the two measurements of diameter [(% $R_T$ - % $R_P$)/% $R_T \times 100$] can be plotted against their means [(% $R_P$ + % $R_T$)/2 $\times 100$] (1). In the scatter diagram the precision and bias of the method can be quantified, and any significant differences between two data points were determined by student t-test. Significant differences between the dose-dependent groups were determined by use of Analysis Of Variance between groups (ANOVA). A probability of $p < 0.05$ was considered to be indicative of a statistically significant difference.

Figure 11D:
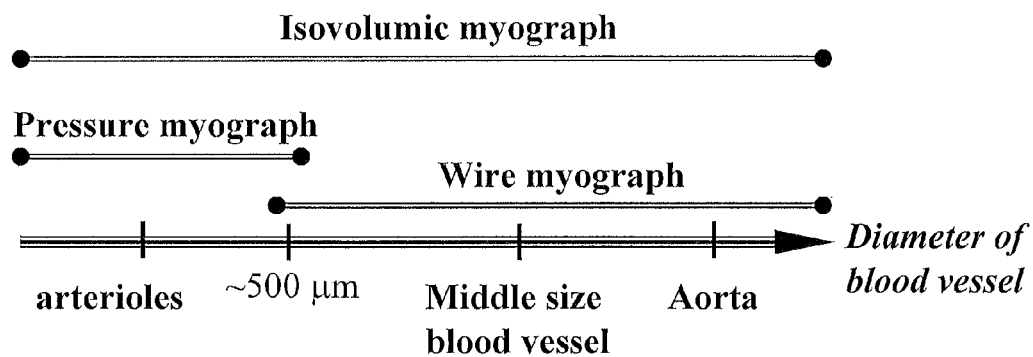
FIG. 11D shows a schematic of the range of applicability (size of vessels) of a wire myograph, a pressure myograph, and an isovolumic myograph, according to the present disclosure.

Results: The isovolumic myograph was used to test mesenteric, femoral and aortic vessels in a consistent manner as opposed to wire and pressure myograph which invoke different methodologies as shown in FIG. 11D. FIG. 11D shows a schematic of the range of applicability (size of vessels) of a wire myograph, a pressure myograph, and an isovolumic myograph of the present disclosure. Since the vessel wall is permeable to water, intraluminal pressure results in a water flux across the vessel wall which causes a gradual drop of baseline pressure in the isovolumic myograph. A microsyringe was used to compensate for the water flux to maintain a constant baseline pressure. FIG. 12 shows the changes in intraluminal pressure determined with isovolumic myography in a femoral artery segment with volume compensation at 38 nl/min to offset the fluid filteration. When a vessel is distended to a higher pressure, a higher compensatory rate is needed to maintain a uniform baseline pressure. Similarly, a thinner-walled vessel requires higher compensatory rate because of increased filtration.

Figure 13A:
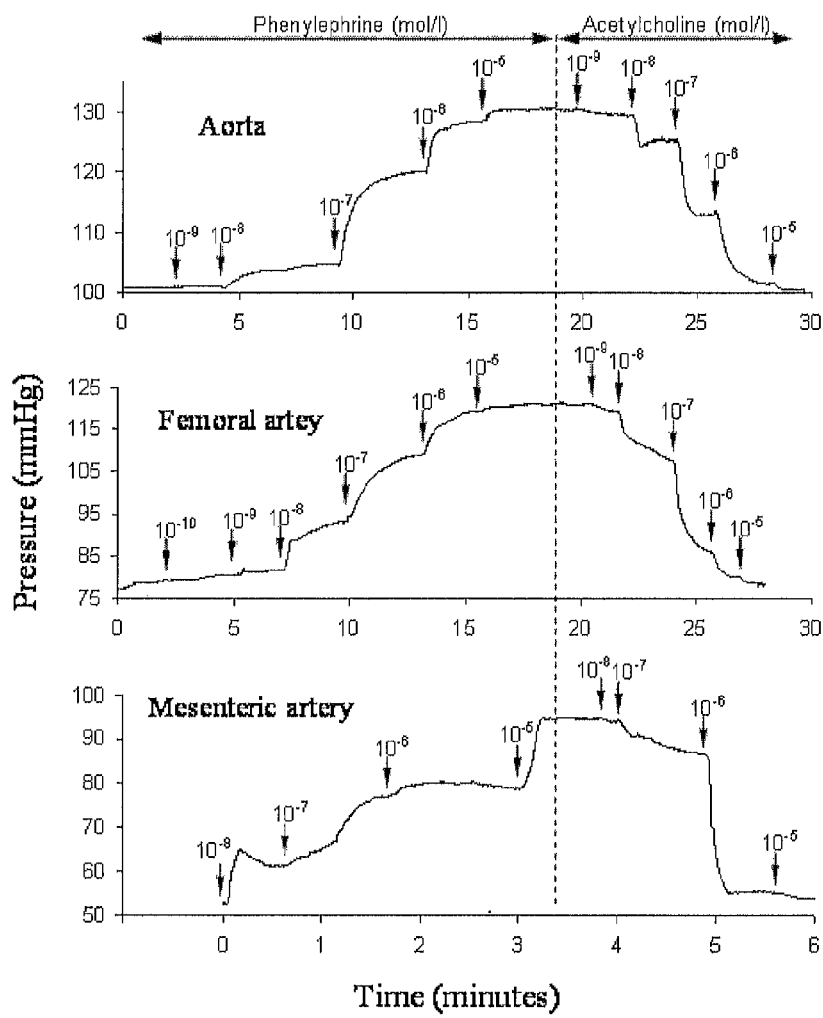
FIG. 13A shows three typical tracing curves of intraluminal pressure in response to pharmacological vasoconstriction and vasorelaxation, according to the present disclosure.
Figure 13B:
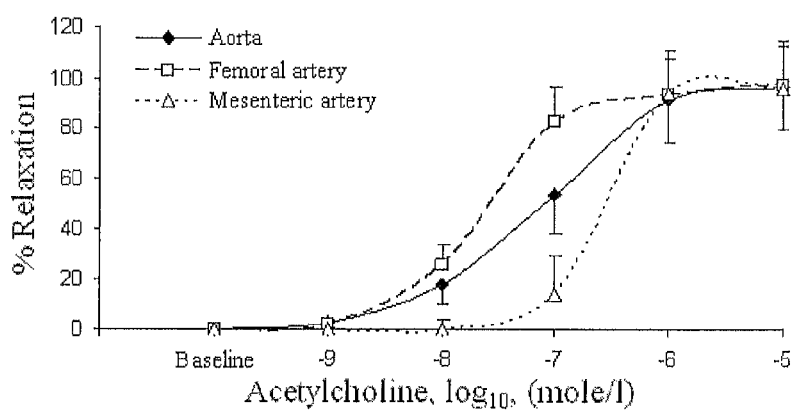
FIG. 13B shows that the percent relaxations of aorta, femoral artery, and mesenteric artery are calculated as the ratio of pressure deference from the tracing curves of intraluminal pressures, according to the present disclosure.

The typical tracing curves of aorta, femoral artery, and mesenteric artery are shown in FIG. 13A. FIG. 13A shows three typical tracing curves of intraluminal pressure in response to pharmacological vasoconstriction and vasorelaxation. The vessel segments were stretched to their in vivo length and inflated to physiological pressure and then stimulated with phenylephrine (mole/l) and acetylcholine (mole/l). The top panel corresponds to the aorta, the middle panel corresponds to the femoral artery, and the bottom panel corresponds to the mesenteric artery. The inflated physiological pressure of aorta, femoral artery, and mesenteric artery were ~100, 70, and 50 mmHg, respectively. The contraction generated from vascular smooth muscle in the three types of arteries caused an increase in intraluminal pressure of 30 to 40 mmHg in response to agonist of PE at $10^{-5}$ mole/l. The dose-dependent vasorelaxations in response to ACh were clearly observed by the stepwise reduced intraluminal pressures as shown in FIG. 13A. The % Relaxation of the three types of arteries was summarized in FIG. 13B, showing that the maximal % Relaxation was identical in the three types of arteries. FIG. 13B shows that percent relaxations of aorta, femoral artery, and mesenteric artery are calculated as the ratio of pressure deference from the tracing curves of intraluminal pressures.

Figure 14A:
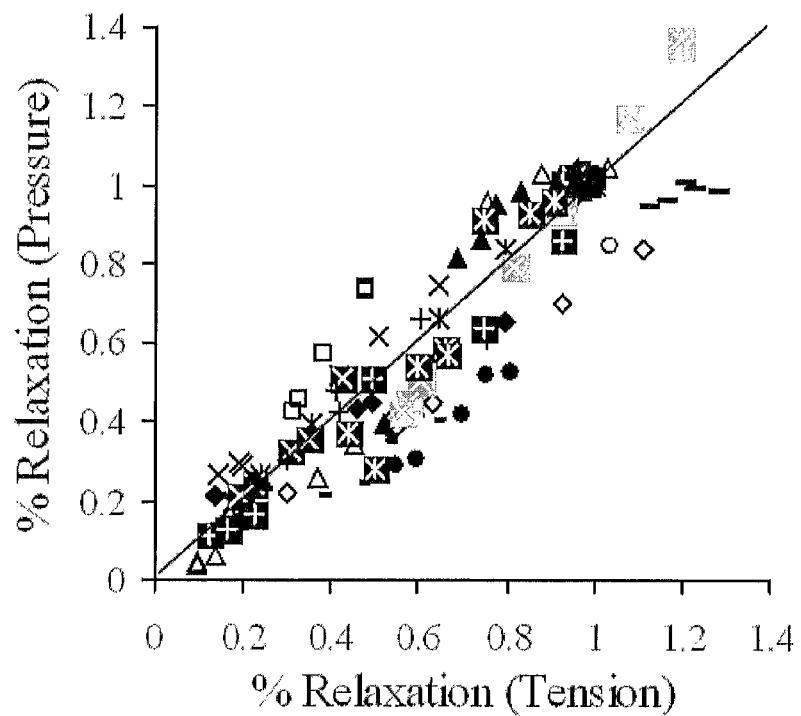
FIG. 14A shows the interrelationship of % Relaxation resulted from circumferential tension and transmural pressure, according to the present disclosure.
Figure 14B:
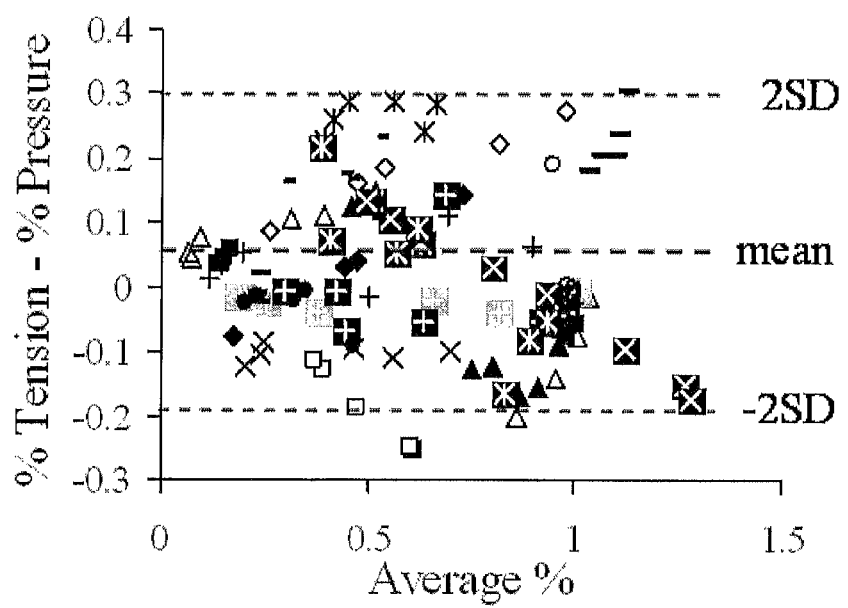
FIG. 14B shows a Bland-Altman plot of percent difference in measurements vs. mean of % Relaxation obtained by the methods referenced by FIG. 14A, according to the present disclosure.

The % Relaxation can be calculated based on both intraluminal pressure and tension. FIG. 14A shows a comparison of the two measurements relative to an identity line. FIG. 14 shows the interrelationship of % Relaxation resulted from circumferential tension and transmural pressure, whereby the empirical relation is expressed as % $R_P = 1.02\%$ $R_T - 0.102$ ($R^2 = 0.99$), wherein % $R_P$ and % $R_T$ represent percentage of pressure and percentage of tension measurements, respectively. A Bland-Altman plot is shown in FIG. 14B, which is the average of two measurements versus difference, and the data are seen to scatter randomly within two standard deviations of the mean of the difference. As shown in FIG. 14B, the Bland-Altman plot of percent difference in measurements vs. mean of % Relaxation obtained by the two methods referenced above. The mean±SD for the data is 0.78±5.0%, and the top and bottom dotted lines represent mean+2SD (10.8%) and mean−2SD (−9.2%), respectively.

The root mean square (rms) is 13.7% of the mean value of the two methods. This analysis shows that pressure is an appropriate surrogate of tension in the calculation of % Relaxation and simplifies the measurements and analysis of vasorelaxation.

Figure 15A:
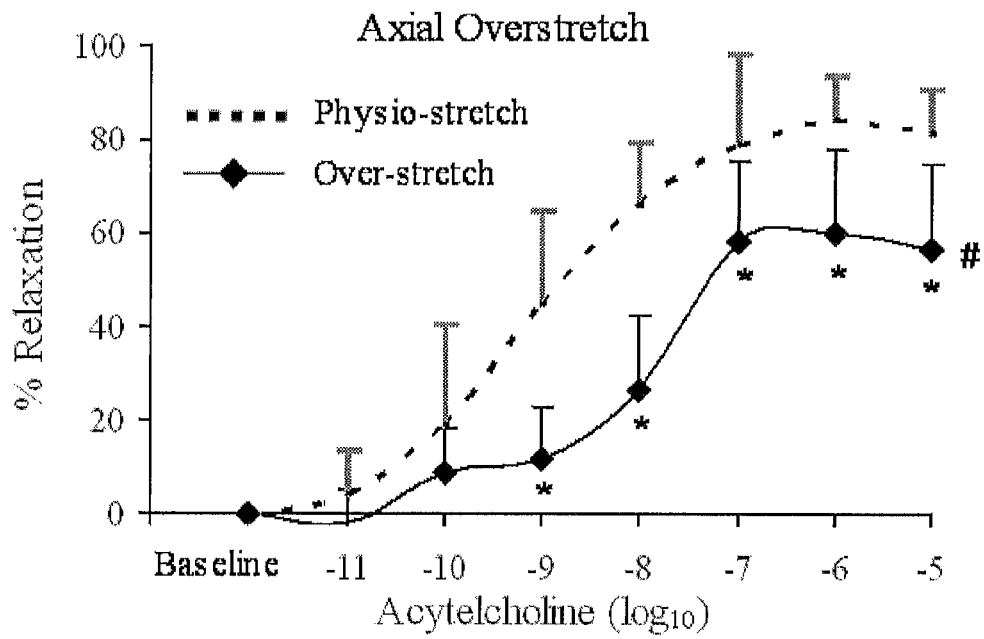
FIGS. 15A and 15B show the effect of axial over-stretch (FIG. 15A) and pressure-overload (circumferential over-stretch, FIG. 15B) on the endothelium-dependent dose-response relation; according to the present disclosure.
Figure 15B:
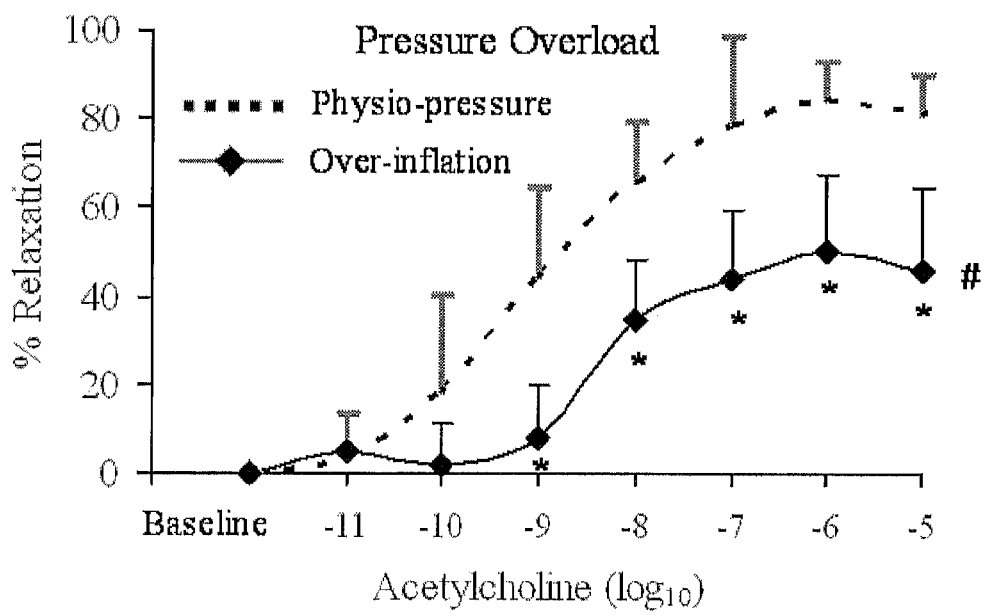

As shown in FIGS. 15A and 15B, the effect of loading perturbation on endothelial-dependent vasodilation in both circumferential and axial directions can be determined. The effect of axial over-stretch (FIG. 15A) and pressure-overload (circumferential over-stretch, FIG. 15B) on the endothelium-dependent dose-response relation are shown. The # shown in FIGS. 15A and 15B indicate a statistical difference ($p<0.05$) of the dose-dependent curve between the physiologic loading and over-physiologic loadings (axial over-stretched or circumferential over-stretched), and the * shown therein indicates significant difference ($p<0.05$) at single dose between physiologic and over-physiologic loadings. As compared with physiologic loading, ACh-induced relaxations in the arteries were attenuated during acute over-inflation (170% of physiologic pressure) and axial over-elongation (118% of physiologic stretch) as shown in FIG. 15. The SNP ($10^{-5}$ mole/l)-induced endothelium-independent relaxations were 96%±8% in physiological loading, 93%±11% in axial over-stretch loading, and 99%±13 in over-inflation (NS). Therefore, the attenuation of ACh-induced vasodilation may be attributed to a decrease in the endothelium-released vasodilators.

As referenced above, a volume-compensated isovolumic myograph has equal sensitivity to aortic, femoral, and mesenteric arterial segments in rats. Hence, the isovolumic myograph provides a unified assay for a functional biomarker of endothelial function (% Relaxation) of small, medium and large vessels as shown in FIG. 11. Such an approach provides consistent testing conditions of all vessels sizes and allows comparisons of different vessels under different pathological conditions as shown in FIG. 13B. Such studies can also show that over-inflation and -elongation cause immediate decrease of endothelium-dependent vasorelaxation. The latter findings underscore the significance of physiological loading on assessment of endothelial function.

In order for a vascular assay to garner utility, it must be simple and easy to use. Accordingly, the following question was addressed: can pressure replace tension to eliminate the need for microscope and only require a pressure transducer? FIG. 14, as referenced herein, shows that this is possible with a 13.7% rms of the mean. Hence, the pressure can be used interchangeably with tension which simplifies future experiments and allows multiple parallel vessel testing. This will provide a higher throughput for vascular physiopathology.

There is no doubt that physical loading influences the reactivity of blood vessel and the response of the endothelium. Ideally, the loading and geometry of vessel segment should mimic physiologic conditions. In a wire myograph, a vessel ring is loaded by hooks to make the loading uniaxial and planar in the circumferential direction while the axial tension is zero. Although the loading is clearly non-physiological, the wire myograph has been a very popular method for vessel reactivity due to its excellent tension measurement sensitivity. As demonstrated here, the disclosure of the present application shows that the endothelium-dependent vasorelaxation can be significantly affected by axial loadings, where axial over-elongation attenuates the endothelium-dependent vasorelaxation as shown in FIG. 15. This observation confirms that the wire myograph is not physiological and may have methodological artifacts.

In contrast to the tension in wire myograph, the vessel diameter is the measurement variable in pressure myograph. The contractile tension of a muscle depends on the number of activated actin-myosin filaments while the contractile dimension depends on the movement between actin and myosin fiber. Based on Hill's equation (tension-velocity relation), the relation between tension and diameter is strongly nonlinear during contraction. Since measurement of either tension or diameter is inadequate to understand active properties of an artery, the wire myograph (tension measurement) and pressure myograph (diameter measurement) are inadequate and comparison between the two methods is difficult due to the different loading patterns and measurement parameters. In order to monitor the tension during vasoreactivity, the isovolumic myograph of the present disclosure has been developed to track the transient tension (pressure) as well as diameter. This development allows both measurements of tension and diameter. In practice, the isovolumic myograph provides consistent results with previous studies but also leads to new observations like those shown in FIG. 15.

The importance of maintaining the blood vessel at physiological load is that the wall tension of an artery may influence vasoreactivity in two ways: vascular smooth muscle and endothelial cells. The alteration of wall tension may activate or inactivate contraction of vascular smooth muscle and the signal pathways of endothelial cells mediated by mechanotransductions such as integrins and G-protein coupled receptors. As shown herein, the effect of perturbations from physiological loading on the vasorelaxation of blood vessel is substantial as shown in FIG. 15, and can be verified The vessel segment in wire myograph is tension free axially in comparison with an in vivo vessel which is stretched axially; the extent of which can vary in hypertension, aging and vessel disease. These investigations provide, for the first time, direct evidence that either acute axial over-elongation or intraluminal over-inflation causes immediate endothelial dysfunction.

Gastric Study

Furthermore, and regarding gastric motility, the disclosure of the present application provides various systems and methods to measure the same.

The effect of gastric distension has important implications for satiety. A hypothesis used leading up to the disclosure of the present application was that distension affects the amplitude and duration of gastric contraction, and that these parameters are largely mediated by efferent vagus activation. A novel isovolumic myograph was developed to test these hypotheses, with the isovolumic myograph isolating the stomach and recording the pressure generated by the gastric contraction in isovolumic conditions. Accordingly, the phasic changes of gastric contractility can be documented.

The animal experiments were performed as follows. Twelve C571/B mice at twelve (12) weeks of age were obtained from an off-site location and were acclimated to the testing facility for approximately one (1) week prior to the start of the study. The animals were housed at 22° C. under a 12-hour light and dark cycle and were given free access to tap water and standard rodent chow. The animals the were anesthetized with xylazine (1 mg/kg, i.p.) and ketamine (9 mg/kg, i.p.) and maintained with xylazine (0.5 mg/kg) and ketamine (4.5 mg/kg) every half hour.

In vivo gastric contractility: Under anesthesia, the abdominal skin and muscle layers of the animal were opened to expose the stomach. The stomach was moistured with warm (37° C.) physiological saline solution (HEPES-PSS in mmole/L: 119 NaCl, 4.7 KCl, 25 $NaHCO_3$, 1.17 $KH_2PO_4$, 1.17 $MgSO_4$, 1.6 $CaCl$, 5.5 Dextrose). The stomach was cannulated with a HEPES-PSS prefilled catheter (ID: 1 mm, OD: 2 mm) which connected to the isovolumic system as shown in FIG. 11A. A 2 mm incision was cut at fundus apex of stomach through which the catheter (OD: 2 mm) was inserted into stomach lumen. The fundus adjacent to the incision was tied on the tube with 6-0 silk suture twice to ensure no leakage. Two ml of HEPES-PSS was gently injected into stomach through the tube to wash out the content. The lower esophageal sphincter and pyloric sphincter were ligated with 6-0 silk suture. The gastric mesentery was untouched to allow the stomach to work in a physiological environment maintaining normal circulation and vagal responses.

Ex vivo gastric contractility. The animals were euthanized by overanesthesia. The stomach was excised quickly and placed in cold HEPES-PSS. The adjacent tissue was dissected with the aid of a stereo microscope. The stomach was allowed to warm up to room temperature (22° C.) slowly in 10-15 min and was transferred to a chamber with HEPES-PSS (22° C.) of the isovolumic myograph. A 2 mm incision was cut at fundus apex of the stomach (fibrosic portion) and a catheter (ID: 1 mm, OD: 2 mm) was inserted into the stomach lumen through the incision. The fundus adjacent to the incision was tied on the catheter with 6-0 suture twice to avoid leakage. A 2 ml HEPES-PSS was gently injected into the stomach through the catheter to wash out the gastric content. Following drainage, the lower esophageal sphincter and pyloric sphinter were ligated with 6-0 silk suture. The stomach in the chamber was warmed to 37° C. slowly (15-20 min) and equilibrated for 30 min at a basal intragastric pressure of about 2 mmHg before distension.

Figure 16A:
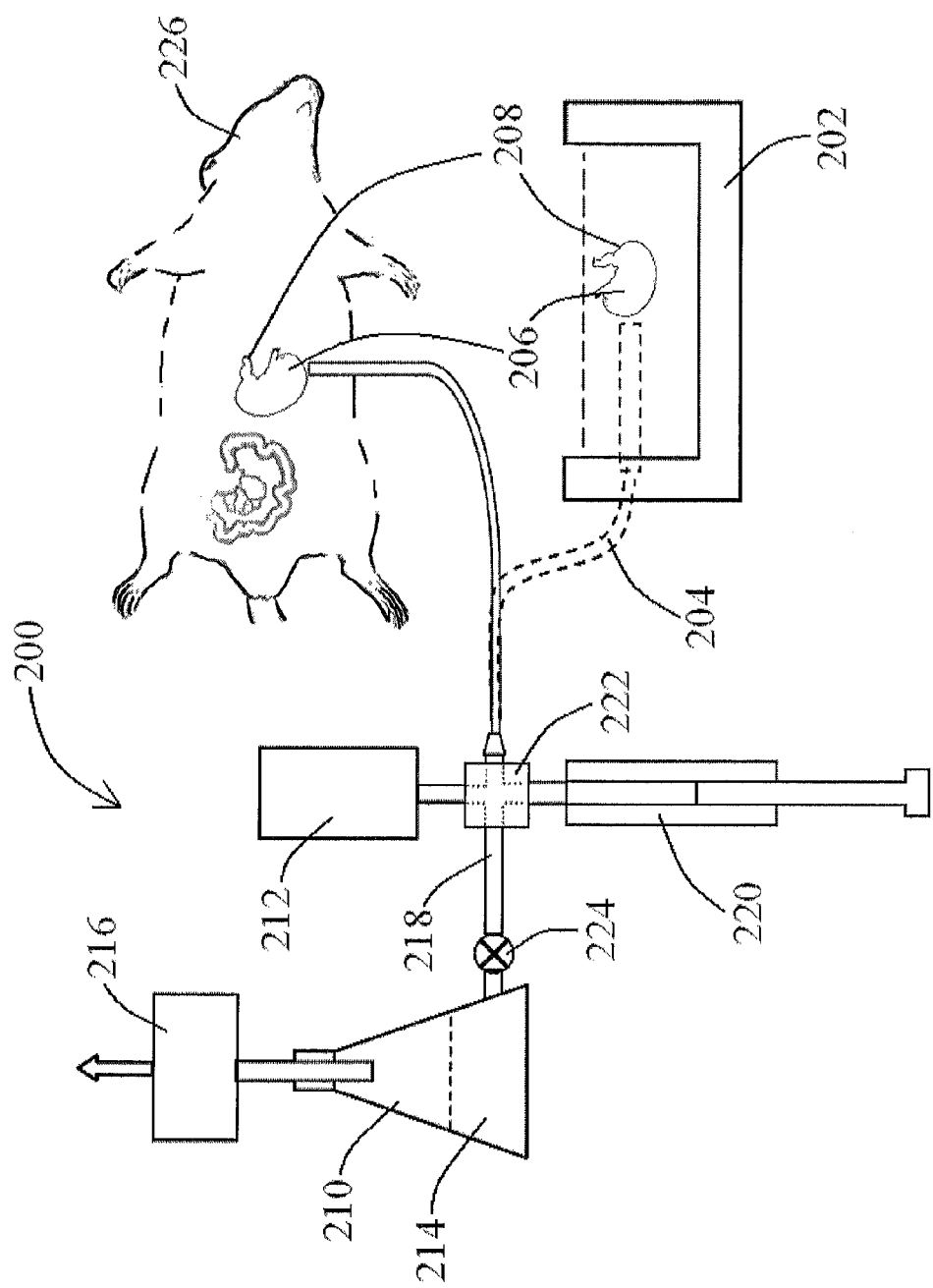
FIG. 16A shows an exemplary in vivo/ex vivo system for detecting a luminal organ response to one or more chemicals, according to at least one embodiment of the present disclosure.

Isovolumic system. An exemplary isovolumic system used for the present study is shown in FIG. 16A. As shown in FIG. 16A, an exemplary ex vivo system 200 comprises a chamber 202 with a catheter 204 on one side wall of the chamber which bridges the lumen 206 of a stomach 208 to inflation flask 210 and pressure transducer 212. As shown in FIG. 16A, system 200 is connected to a stomach 208, but in various other embodiments, system 200, and related methods as referenced herein, may be connected to various other mammalian organs, such as the trachea, lymph vessels, lymph ducts, urinary bladders, ureters, gall bladders, bile ducts, hepatic ducts, intestines, and the like, whereby contraction can be generated by surrounding smooth muscle.

Chamber 202, in at least one embodiment, may contain HEPES-PSS maintained at 37° C. using a heater (not shown), for example. Inflation flask 210, which in at least one embodiment comprises a 50 mL flask, having PSS 214 therein is connected to a pressure regulator 216 so that a stomach 208, for example, can be inflated/distended to the desired pressure. The catheter 204, a solid state pressure transducer 212 (SPR-524, Microtip catheter transducer, Millar Inc, Texas), a tube 218 to inflation flask 214, and a compensatory microsyringe 220 were assembled using a four-way connector 222. A compensatory microsyringe 220 (50 µl gastight microsyringe, UltraMicroPump III, and Micro 4™ microsyringe controll, World Precision Instruments, USA) was used to stabilize the baseline of the pressure since water transport across the gastric wall reduces the intragastric pressure. The clamping of tube 218 between inflation flask 210 and four-way connector 222, by way of stopcock 224, achieved isovolumic conditions, i.e., intragastric volume was constant. In at least one embodiment, a CCD camera on a microscope 2, such as shown in FIG. 1, and an image processing system (such as the computer shown in FIG. 5A), may be used to capture the gastric geometry. As stomach 208 was inflated to a desired pressure (e.g., 5 mmHg, 10 mmHg, etc.), stopcock 224 was closed and the gastric contraction or relaxation was reflected by the variation of intragastric pressure recorded with solid state pressure transducer 212. The isovolumic system 200 can also record the periodic contractions of stomach 208 by the periodic variations of pressure.

In at least an additional embodiment of a system 200 of the present disclosure, various components of said system 200 may be used in connection with measurements of in vivo gastric contractility as referenced herein, including, but not limited to, those components used in the various embodiments of system 100 referenced herein. For example, and as shown in FIG. 16A, catheter 204 may connect directly to a stomach of a mammal 226 under anesthesia, so that measurements can be taken in a in physiological environment maintaining normal circulation and vagal responses. Furthermore, an exemplary system 200 may include any number of other components useful for the same, such as various additional tubes and clamps to facilitate connection of the various components. Furthermore, chamber 202 may include any number of solutions, including HEPES, HEPES-PSS, PSS, and/or any number of other solutions to facilitate the aforementioned measurements.

Gastric contractility in response to mechanical stimulation. The mechanical stimulation of stomach 208 was induced by an intragastric inflation pressure. The gastric contraction was quantified by the intragastric pressure under isovolumic condition and the contractility was characterized with the amplitude and period of the pressure waveforms. Stomach 208 was inflated to a desired pressure by a pressure regulator 216 connected to flask 210 as referenced above. The clamping of the tube 218 between the inflation flask 210 and the four-way connector 222 maintained a constant volume of solution in the gastric lumen (isovolumic condition). The compensatory microsyringe 220 maintains isovolumic conditions at, for example, an infusion rate of 1-3 µl/min. The data was discarded if the rate was larger than 10 µl/min since this implied damage (leakage) of the gastric wall. At isovolumic conditions, the variations of intragastric pressure was recorded with a data acquisition system (Biopac, MP100, Houston, Tex.). The amplitude, frequency, and contractile duration of pressure waveforms were analyzed to characterize the gastric contractility.

Protocol of mechanical stimulation. The intragastric pressure was increased stepwise to 2, 5, 10, 15, 20, 30, 40, and 50 mmHg at a rate of 0.06 ml/min, respectively. The gastric contraction at isovolumic condition was recorded as the variation of the pressure at each individual inflation pressure. This protocol was applied to both in vivo and ex vivo stomach 208. In the experiment of ex vivo stomach, acetylcholine ($10^{-6}$ mole/l) was used to elicit non-neuroactive contraction of gastric smooth muscle at intragastric pressure of 50 mmHg to evaluate contractility of gastric smooth muscle.

Figure 16B:
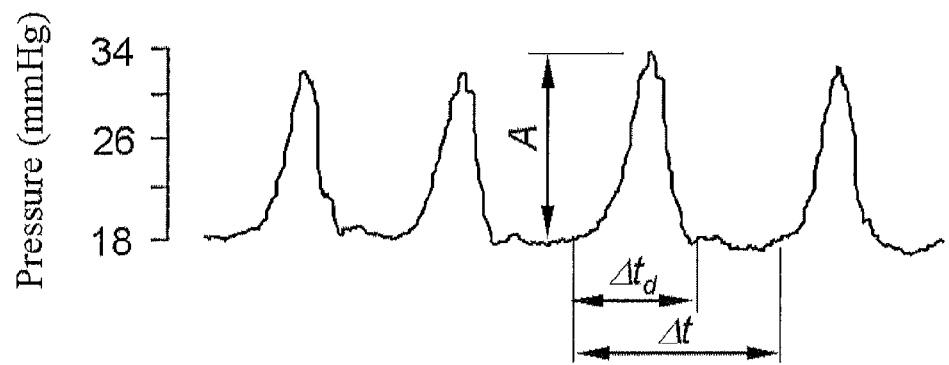
FIG. 16B shows a graph of typical pressure waves relating to gastric contraction obtained by an exemplary method and/or system of the present disclosure.

Data Analysis and Statistics. FIG. 16B illustrates the definition of the parameters used in the analysis, showing typical pressure waves relating to gastric contraction. The gastric contractile amplitude (A) was indicated by the amplitude of the variation of pressure. The gastric contractile period (Δt) was defined as the interval from one pressure waveform to the next pressure waveform. The gastric contractile duration ($\Delta t_d$) was defined as the interval from pressure rise to fall.

The data is presented as mean±SD. Significant differences between groups were determined by student t-test. Significant differences between the in vivo and ex vivo groups were determined by use of Analysis Of Variance (ANOVA) between groups. A probability of $p<0.05$ was considered indicative of a statistically significant difference.

Figure 16C:
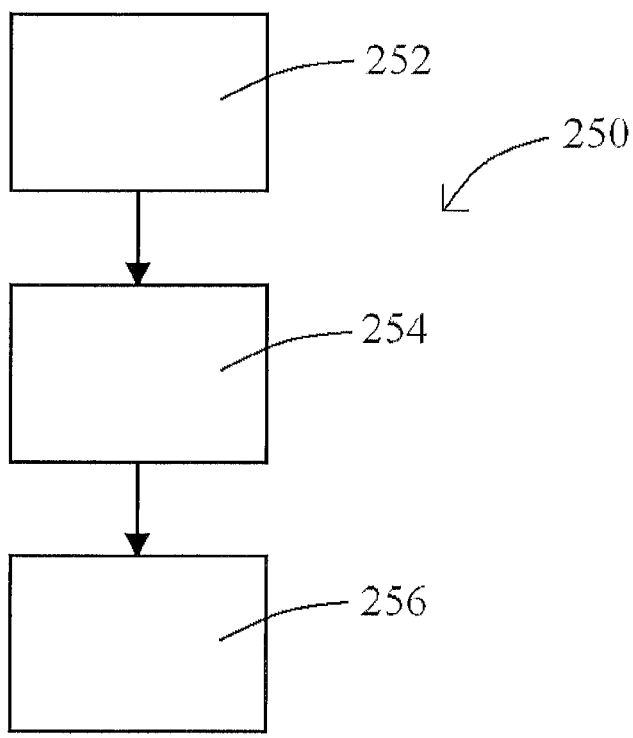
FIG. 16C shows method for detecting a luminal organ response to mechanical stimulation, according to the present disclosure.

Steps of an exemplary method for detecting a luminal organ response to mechanical stimulation of the present disclosure is shown in FIG. 16C. As shown in FIG. 16C, exemplary method 250 comprises the steps of maintaining a luminal organ at a first internal pressure (an exemplary maintenance step 252), increasing the first internal pressure of the luminal organ (an exemplary pressure increase step 254), and measuring a first organ parameter change in response to the increase in internal pressure (an exemplary parameter change measurement step 256). In an exemplary embodiment of method 250, the luminal organ is positioned within a chamber for receiving a fluid, and wherein the fluid is in contact with the luminal organ.

In an exemplary embodiment of a method 250 of the present disclosure, maintenance step 252 comprises positioning a conduit within an incision of the luminal organ so that a lumen of the conduit is in fluid communication with a lumen of the luminal organ, and introducing a liquid through the conduit into the lumen of the luminal organ until the luminal organ achieves the first internal pressure. In at least one embodiment of a method 250, pressure increase step 254 comprises introducing a fluid from the conduit into the lumen of the luminal organ.

In additional exemplary maintenance step 252 of an exemplary method 250 of the present disclosure comprises the steps of positioning the luminal organ within a system for detecting a luminal organ response, introducing a fluid into a lumen of the luminal organ until a desired first internal pressure is achieved, and closing at least part of the system so that fluid is not permitted to escape the luminal organ through a component of the system.

In at least one embodiment of a method 250 of the present disclosure, and as referenced in detail herein, the first organ parameter change is selected from the group consisting of a decrease in luminal organ diameter, an increase in luminal organ diameter, a decrease in internal luminal organ pressure, an increase in internal luminal organ pressure, and an increase in gastric contractility. In an exemplary method 250, parameter change measurement step 256 is performed using a pressure transducer, a microscope, and/or a camera. In an exemplary embodiment, maintenance step 252 comprises injecting additional fluid into a lumen of the luminal organ in response to luminal organ leakage through a wall of the luminal organ. The additional fluid may be injected using a volume compensator.

In an exemplary method 250 of the present disclosure, the luminal organ is present within a living mammal while various method steps are being performed. In another exemplary embodiment, and when the stomach is present within a living mammal, the attenuation of gastric contractility is mediated by efferent vagus activation as referenced in detail herein. In yet another exemplary embodiment, such a method 250 may be used in connection with intestinal studies as referenced below.

Figure 17:
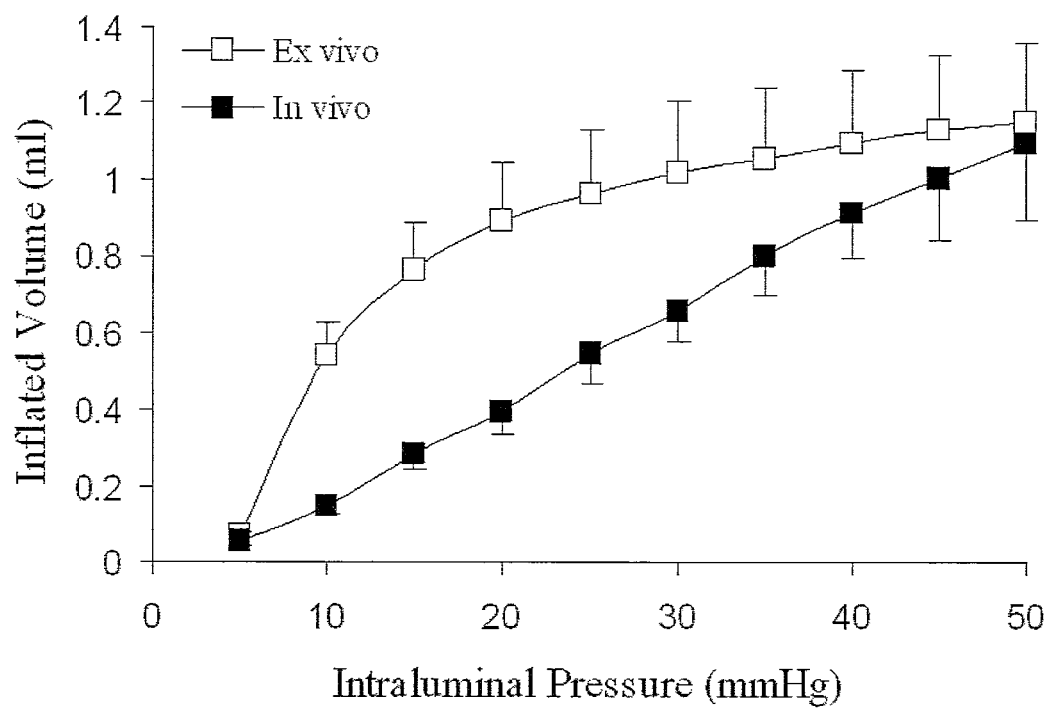
FIG. 17 shows a graph of the relationship between gastric capacity and inflation pressure for various conditions, according to the present disclosure.

Results. The intragastric pressure and gastric volume in both in vivo and ex vivo are shown in FIG. 17, which reflects the global distension (compliance) of the stomach. The in vivo gastric volume was significantly different from the ex vivo volume. The ex vivo gastric volume increased in low pressure range (5-20 mmHg) while in vivo gastric volume increased almost linearly.

Figure 18A:
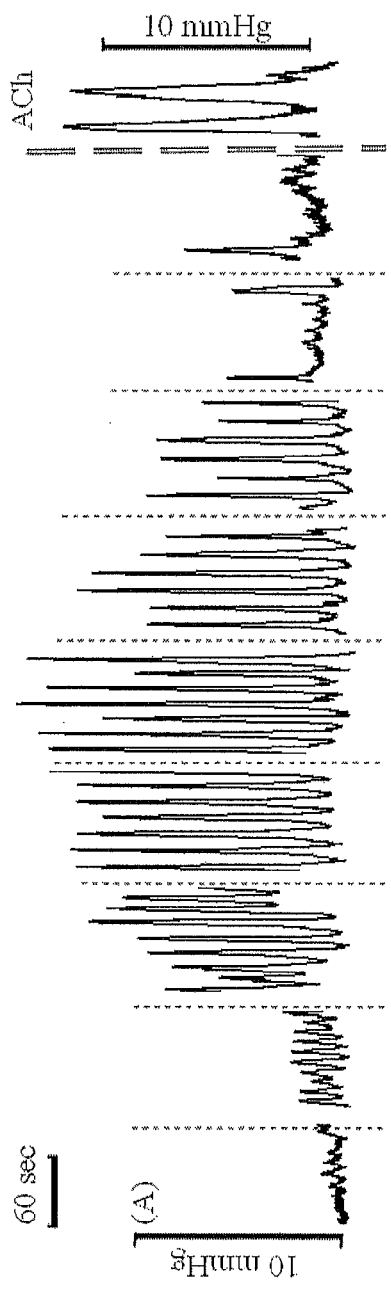
FIGS. 18A and 18B show graphs of intragastric pressure waveforms during gastric contraction, according to the present disclosure.
Figure 18B:
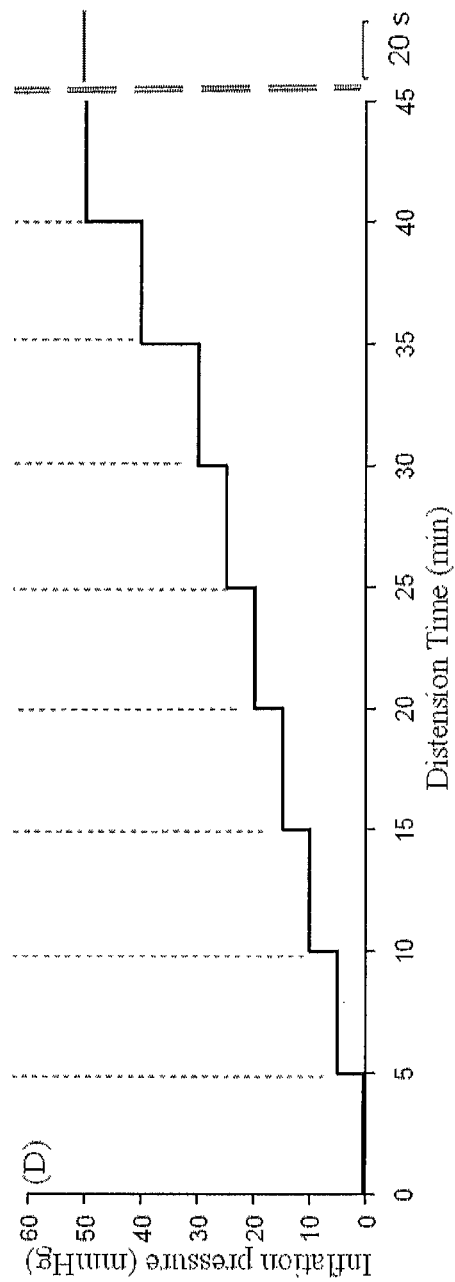

The intragastric pressure waveforms during gastric contraction are shown in FIG. 18A. The variation of the pressure reflects the gastric contractility which is characterized by three parameters: contractile amplitude, duration, and period. The in vivo amplitude of gastric contraction increased from 1.6 mmHg to 12.5 mmHg when the inflation pressure changed from 2 mmHg to 30 mmHg, respectively, as shown in FIG. 18A. FIG. 18B shows inflation pressure vs. distension time in stepwise fashion.

Figure 19A:
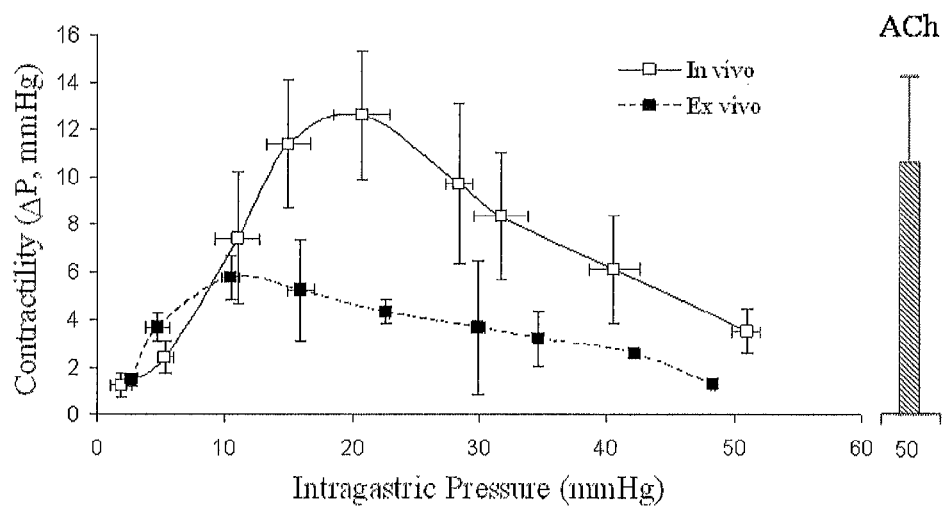
FIGS. 19A and 19B show graphs of amplitudes of the contractile waves for various conditions, according to the present disclosure.
Figure 19B:
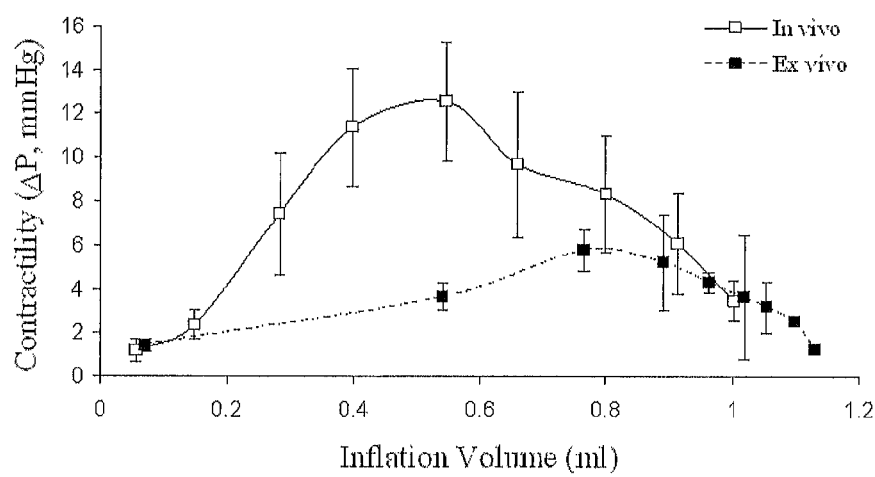

The contractility relation is shown in FIGS. 19A and 19B both as a function of inflation pressure (FIG. 19A) and volume (FIG. 19B). The contractility increases with an increase in inflation pressure of volume and reaches a maximum for the in vivo condition. FIGS. 19A and 19B show the amplitude of the contractile waves for various conditions. FIG. 19A shows the amplitude represented as a function of intragastric pressure, and FIG. 19B shows the amplitude represented as a function of inflation volume. The in vivo amplitude then decreases from 12.5 to 3.3 mmHg (FIG. 19A) when the inflation pressure further increases from 30 to 50 mmHg. In ex vivo, the gastric contractile amplitude is significantly lower than that in in vivo at every inflation pressure. At 50 mmHg inflation pressure, the ex vivo contraction is completely abolished. It was noted that the contraction stimulated by the external administration of ACh (the right columns of FIGS. 18A and 19A, for example), however, is still high, which suggests that the efferent nervous activated contraction fails under high distension and may be the cause of the attenuation of contractility.

Figure 20A:
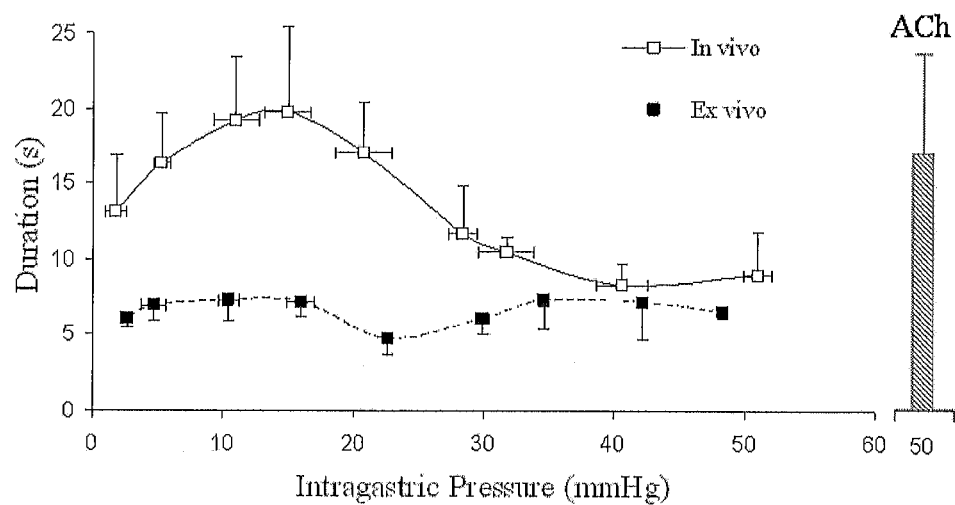
FIGS. 20A and 20B show graphs of durations of gastric contractility in vivo and ex vivo, according to the present disclosure.
Figure 20B:
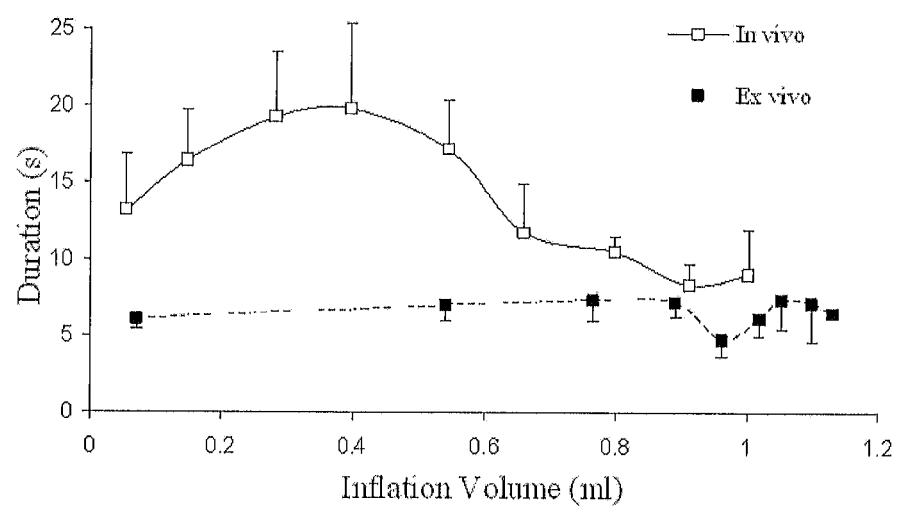

The durations of the gastric contractility in vivo and ex vivo and under two gastric banding conditions are presented in FIGS. 20A and 20B as a function of intragastric pressure (FIG. 20A) and inflation volume (FIG. 20B). The duration indicates the sustained interval of a single contraction wave. The in vivo duration was significantly larger than the ex vivo duration when the inflation pressure was below 35 mmHg or inflation volume was below 0.7 ml. The in vivo duration reached a maximum between 10 to 20 mmHg or 0.3 to 0.5 ml of inflation pressure or volume, respectively. The ex vivo duration did not significantly change with the inflation.

Figure 21A:
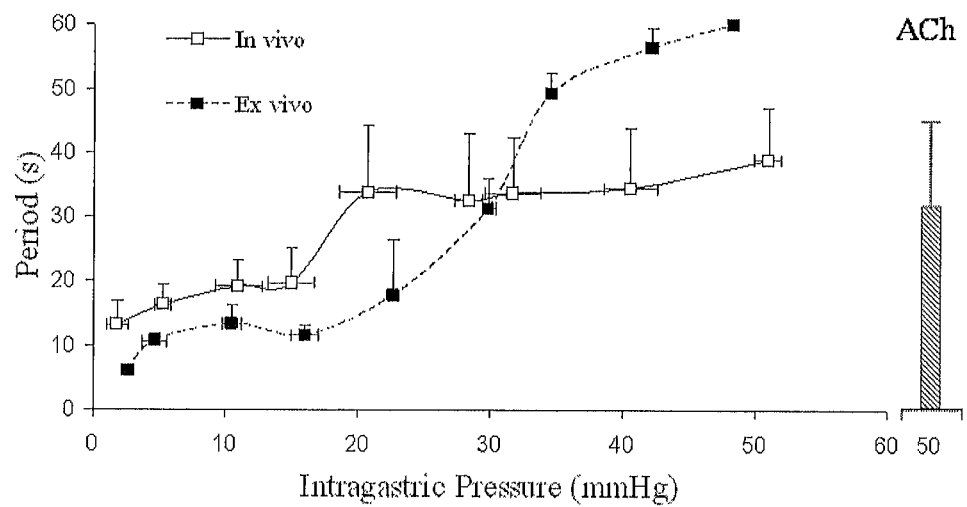
FIGS. 21A and 21B show graphs of the period of gastric contractility in vivo and ex vivo, according to the present disclosure.
Figure 21B:
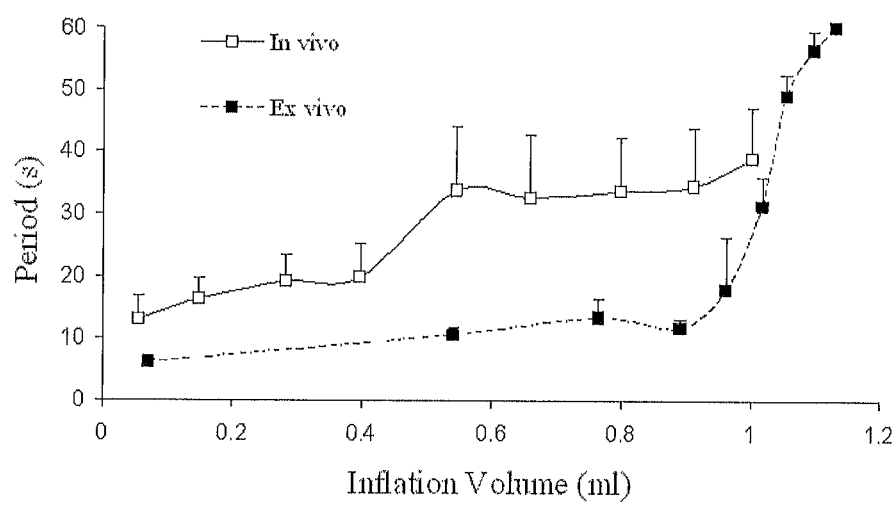

The period of the gastric contractility in vivo and ex vivo are shown in FIGS. 21A and 21B as a function of intragastric pressure (FIG. 21A) and volume (FIG. 21B). The period indicates the contractile frequency. The results show that the period was similar in both in vivo and ex vivo preparation and increases with inflation.

As referenced above, and in summary, the isovolumic myography system 200 was used to assess gastric contractility in terms of amplitude, duration, and period. The in vivo preparation was designed to detect the efferent neurogenic contraction and ex vivo preparation was designed to measure the efferent-independent contraction. The in vivo contractile amplitude and duration were significantly larger than those in ex vivo, indicating that contractile amplitude and duration may be efferent neurogenic. The similar period in in vivo and ex vivo preparation indicates that contractile period may be efferent-independent.

Gastric contractility is closely coupled to the mechanosensitivity located in gastric wall. The myogenic response of gastric smooth muscle and efferent neurogenic contraction are regulated by mechanoreceptors and afferent and efferent vagus nerves. The relation between afferent vagus signals and gastric distension was identified decades ago. The mechanoreceptors in gastric wall are primary sensors of mechanical stimulation. The efferent (motor) vagus signals are responses of the central nervous system to the afferent (sensory) vagus stimulation. One of the physiological functions of efferent vagus signals is to regulate the gastric contractility. Hence, the gastric contractility reflects the activation of an efferent vagus nerve.

As referenced herein, gastric contractility was evaluated in an ex vivo preparation which excludes efferent vagus regulation. In the ex vivo stomach, the nerve fibers are excised and damaged, and hence there is a loss of efferent vagus signals which appears to be significant for mechanical distension-induced contractility. The ex vivo contractility of gastric smooth muscle was significantly attenuated due to the absence of efferent vagus signals. The strong in vivo contractility reflects the efferent vagus activation in response to mechanical stimulation sensed by afferent vagus nerves. The role of duration is noted as it may reflect the efferent vagus activation. The duration of in vivo contraction varies with mechanical stimulation whereas the duration of ex vivo contraction is largely unchanged in response to mechanical stimulation. The latter implies that the duration is regulated by the central nervous system. In contrast, the period seems to be independent of vagus nerve activation since both in vivo and ex vivo periods increase during the increase in distension.

An exemplary isovolumic myograph of the present disclosure (system 200) was used to evaluate the gastric global contractility. The regional contraction, however, was not measured. Since the gastric contractile wave is generated in the lower stomach, the gastric tone (basal pressure) in the fundus and upper body was not characterized herein. The studies referenced in the present disclosure introduced a novel isovolumic myograph to understand the contractility of the stomach. The in vivo and ex vivo gastric contractility in response to distension (inflation) provides evidence that gastric motility can be regulated by the central nervous system.

Intestinal Study

The disclosure of the present application also provides various systems and methods for determining intestinal contraction in response to the stimulation of inflation. In-vivo and ex-vivo protocols were used to verify the effect of extrinsic nervous system and intrinsic nervous regulation on the motility, respectively. The duodenum and colon of mouse were involved in the exemplary study detailed below.

The animal experiments were performed as follows. Twelve C571/B mice at 24 weeks of age were obtained from Charles River. The animals were acclimated to the facility for approximately one (1) week prior to the start of the study. The animals were housed at 22° C. under a 12-hour light and dark cycle and were given free access to tap water and standard rodent chow. The animals were anesthetized with xylazine (1 mg/kg, i.p.) and ketamine (9 mg/kg, i.p.) and maintained with xylazine (0.5 mg/kg) and ketamine (4.5 mg/kg) every half hour. The animal experiments were performed in accordance with the guidelines of Institute of Laboratory Animal Research Guide, Public Health Service Policy, Animal Welfare Act, and an approved IACUC protocol.

In-vivo intestinal contractility. Under anesthesia, the abdominal skin and muscle layers of the animal were opened to expose either the duodenum or the colon. The intestine was moistured with warm (37° C.) physiological saline solution (HEPES-PSS in mmole/L: 119 NaCl, 4.7 KCl, 3 HEPES acid, 2.3 HEPES sodium salt, 1.17 $MgSO_4$, 1.6 CaCl, 5.5 Dextrose). The intestine was cannulated with a HEPES-PSS pre-filled catheter (ID: 1 mm, OD: 2 mm) which connected to the isovolumic system as shown in FIG. 11A. A 2 mm incision was cut at the oral intestine where the catheter (OD: 2 mm) was inserted into the intestinal lumen. The incision was tied on the tube with 6-0 silk suture twice to ensure no leakage. Two ml of HEPES-PSS was gently injected into the intestine through the tube to wash away the content. Another 6-0 silk suture was tied 11 mm away towards the anal intestine from the cannulation. The intestinal mesentery was untouched to allow the intestine to work in a physiological environment maintaining normal circulation and vagal responses.

Ex-vivo intestinal contractility. The animals were euthanized by overanesthesia. Either the duodenum or the colon was excised quickly and placed in cold HEPES-PSS. The adjacent tissue was dissected with the aid of a stereo microscope. The intestine was allowed to warm up to room temperature (22° C.) slowly in 10-15 min and was transferred to a chamber with HEPES-PSS (22° C.) of the isovolumic myograph. The two ends of the intestine were cannulated to the connectors (ID: 1 mm, OD: 2 mm) in the chamber of the isovolumic myograph. The content in the intestine was gently rinsed with HEPES-PSS. The intestine in the chamber was warmed to 37° C. slowly (15-20 min) and equilibrated for 30 min at a basal pressure of about 1 mmHg before distension.

Figure 22:
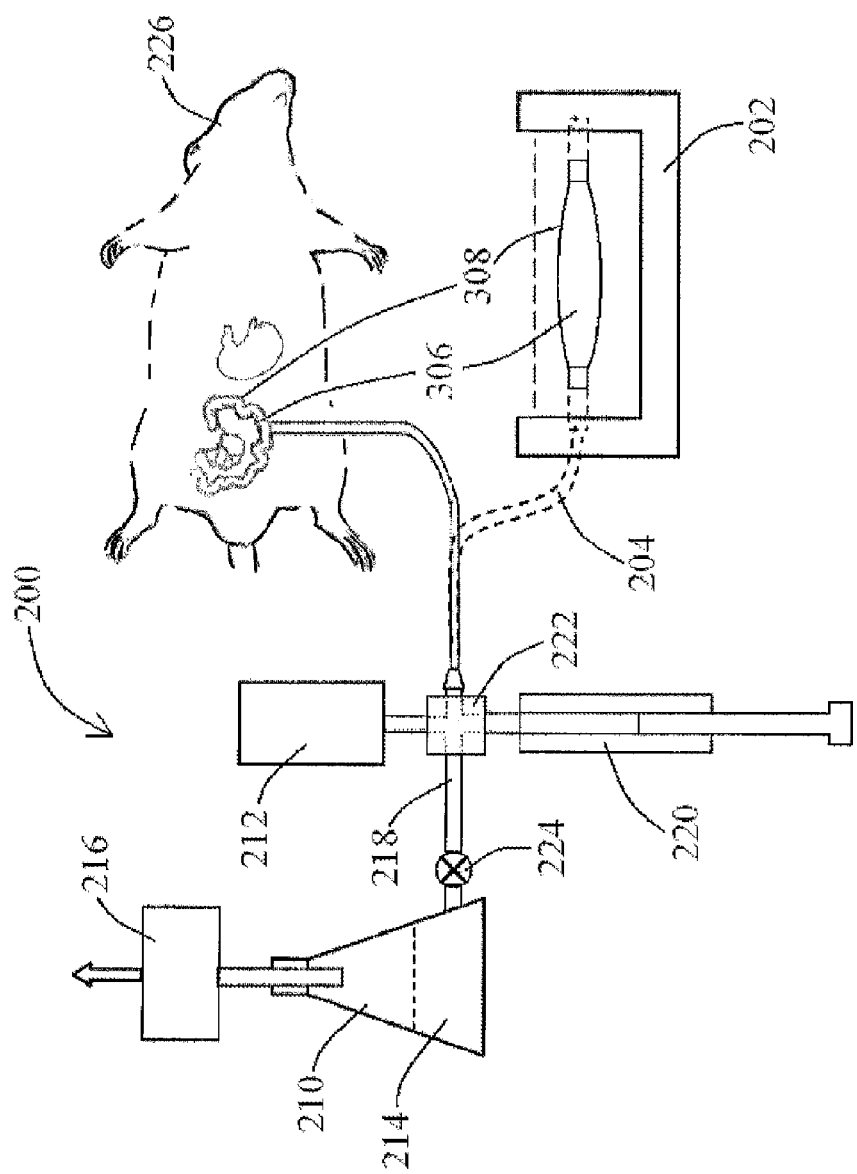
FIG. 22 shows an exemplary in vivo/ex vivo system for detecting a luminal organ response to one or more chemicals, according to at least one embodiment of the present disclosure.

Isovolumic system. An exemplary isovolumic system used for the present study is shown in FIG. 22. As shown in FIG. 22, an exemplary ex vivo system 200 comprises a chamber 202 with a catheter 204 on one side wall of the chamber which bridges the lumen 306 of an intestine 308 to inflation flask 210 and pressure transducer 212. As shown in FIG. 16A, system 200 is connected to intestine 308, but in various other embodiments, system 200, and related methods as referenced herein, may be connected to various other mammalian organs, such as the stomach, trachea, lymph vessels, lymph ducts, urinary bladders, ureters, gall bladders, bile ducts, hepatic ducts, and the like, whereby contraction can be generated by surrounding smooth muscle.

Chamber 202, in at least one embodiment, may contain HEPES-PSS maintained at 37° C. using a heater (not shown), for example. Inflation flask 210, which in at least one embodiment comprises a 50 mL flask, having PSS 214 therein is connected to a pressure regulator 216 so that intestine 308, for example, can be inflated/distended to the desired pressure. The catheter 204, a solid state pressure transducer 212 (SPR-524, Microtip catheter transducer, Millar Inc, Texas), a tube 218 to inflation flask 214, and a compensatory microsyringe 220 were assembled using a four-way connector 222. A compensatory microsyringe 220 (50 µl gastight microsyringe, UltraMicroPump III, and Micro 4™ microsyringe controll, World Precision Instruments, USA) was used to stabilize the baseline of the pressure since water transport across the intestinal wall reduces the intraluminal pressure. The clamping of tube 218 between inflation flask 210 and four-way connector 222, by way of stopcock 224, achieved isovolumic conditions, i.e., intragastric volume was constant. In at least one embodiment, a CCD camera on a microscope 2, such as shown in FIG. 1, and an image processing system (such as the computer shown in FIG. 5A), may be used to capture the intestinal geometry, including intestinal diameter. As intestine 308 was inflated to a desired pressure (e.g., 5 mmHg, 10 mmHg, etc.), stopcock 224 was closed and the intestinal contraction or relaxation was reflected by the variation of intraluminal pressure recorded with solid state pressure transducer 212. The isovolumic system 200 can also record the periodic contractions of intestine 308 by the periodic variations of pressure. Additional features/elements of isovolumic system 200 of the present disclosure may also apply to the exemplary system 200 shown in FIG. 22.

Intestinal contractility in response to mechanical stimulation. The mechanical stimulation of intestine 308 was induced by an intragastric inflation pressure. The intestinal contraction was quantified by the intraluminal pressure under isovolumic condition and the contractility was characterized with the amplitude and period of the pressure waveforms. Intestine 308 was inflated to a desired pressure by a pressure regulator 216 connected to flask 210 as referenced above. The clamping of the tube 218 between the inflation flask 210 and the four-way connector 222 maintained a constant volume of solution in the intestinal lumen (isovolumic condition). The compensatory microsyringe 220 maintains isovolumic conditions at, for example, an infusion rate of 0.6-2.3 µl/min. The data was discarded if the rate was larger than 5 µl/min since this implied damage (leakage) of the intestinal wall. At isovolumic conditions, the variations of intraluminal pressure was recorded with a data acquisition system (Biopac, MP100, Houston, Tex.). The amplitude, frequency, and contractile duration of pressure waveforms were analyzed to characterize the intestinal contractility.

Protocol of mechanical stimulation. The intraluminal pressure was increased stepwise to 2, 5, 10, 15, 20, 30, 40, and 50 (colon only) mmHg at a rate of 0.05 μml/min, respectively. The intestinal contraction at isovolumic condition was recorded as the variation of the pressure at each individual inflation pressure. This protocol was applied to both in vivo and ex vivo intestine 308. In the experiment of ex vivo intestine, acetylcholine ($10^{-6}$ mole/l) was used to elicit non-neuroactive contraction of intestinal smooth muscle at intraluminal pressure of 40 mmHg (duodenum) or 50 mmHg to evaluate contractility of intestinal smooth muscle.

Data Analysis and Statistics. The data is presented herein as mean±SD. Significant differences between groups were determined by student t-test. Significant differences between the in vivo and ex vivo groups were determined by use of Analysis Of Variance (ANOVA) between groups. A probability of $p<0.05$ was considered indicative of a statistically significant difference.

Figure 23A:
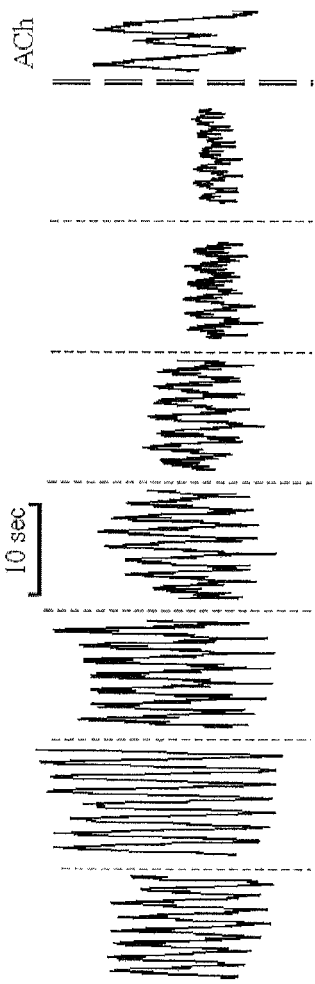
FIGS. 23A, 23B, and 23C show graphs of intraluminal waveforms during duodenal contraction, according to the present disclosure.
Figure 23B:
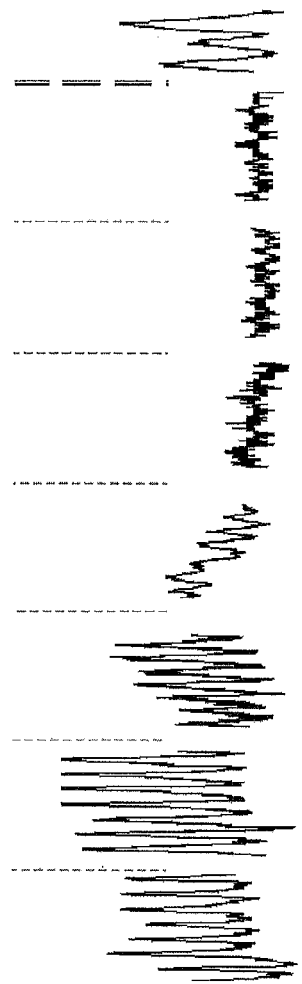
Figure 23C:
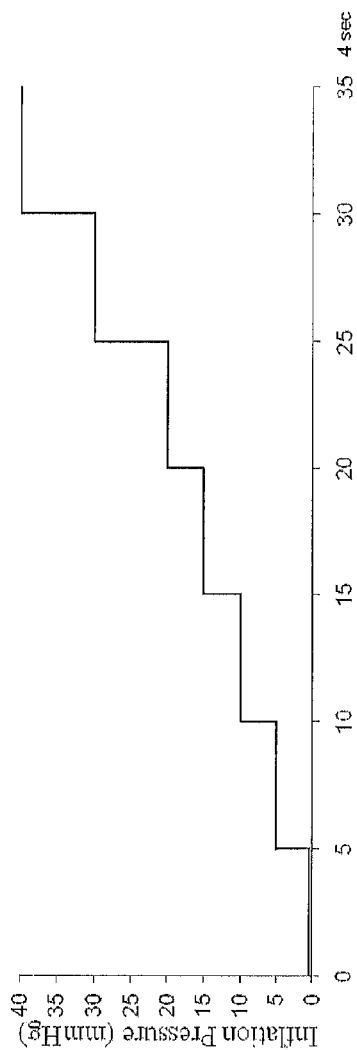

Results. The intraluminal pressure waveforms during duodenal contraction are shown in FIGS. 23A-23C, which clearly show that the amplitudes of intraluminal pressure altered with the inflation pressure. FIG. 23A shows in vivo contractile waves, while FIG. 23B shows ex vivo contractile waves. FIG. 23C represents the inflation protocol used to test the stretch-elicited contractility. The amplitude reached to maximum in all conditions at 5 mmHg of inflation pressure and suppressed down to minimum when inflation pressure increased up to 40 mmHg. The amplitude of the intraluminal pressure reflects the intestinal contractility.

Figure 24A:
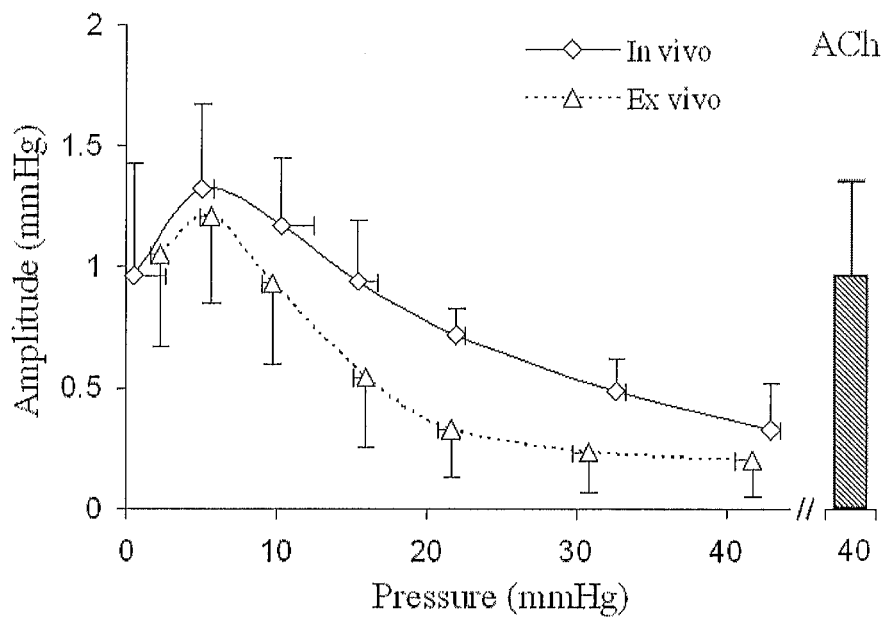
FIGS. 24A and 24B show graphs of amplitude and diameter, respectively, for various conditions, according to the present disclosure.
Figure 24B:
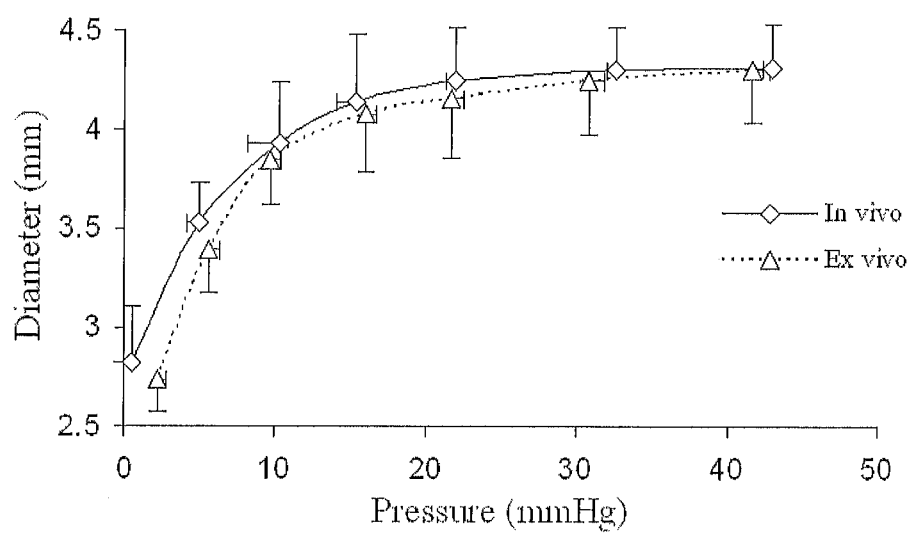

The duodenal contractility is shown in FIGS. 24A and 24B as a function of inflation pressure, with FIG. 24A relating to amplitude (in mmHg) and FIG. 24B relating to diameter (in mm). The in-vivo contractility increased from 0.9 mmHg to 1.4 mmHg while the inflation pressure increased from 1 mmHg to 5 mmHg. Then, the duodenal contractility decreased significantly down to 0.4 mmHg when the inflation pressure further increased from 5 mmHg to 40 mmHg. The ex-vivo duodenal contractility linearly decreased with the increase in inflation pressure. The ex-vivo duodenal contractility was significantly attenuated in comparison with the in-vivo contractility.

The results identified above indicate that the inflation pressure higher than 5 mmHg may be considered an inhibitory role in duodenal motility. The local neuro-regulation may be major role since the trend lines of the in-vivo and ex-vivo contractility are similar. The central nervous regulation in in-vivo contractility seems superimposing a high baseline on the ex-vivo contractility. The smooth muscle contraction stimulated by ACh, however, is still similar to maximum contractility of the in-vivo state, which suggests that neuroactive contraction fails under high distension.

The in-vivo and ex-vivo relationship of inflation pressure and duodenal diameter are shown in FIG. 24B, which reflects the circumferential distensibility of the duodenum. The in-vivo circumferential distensibility was not significantly different to the ex-vivo one ($p>0.05$).

Figure 25A:
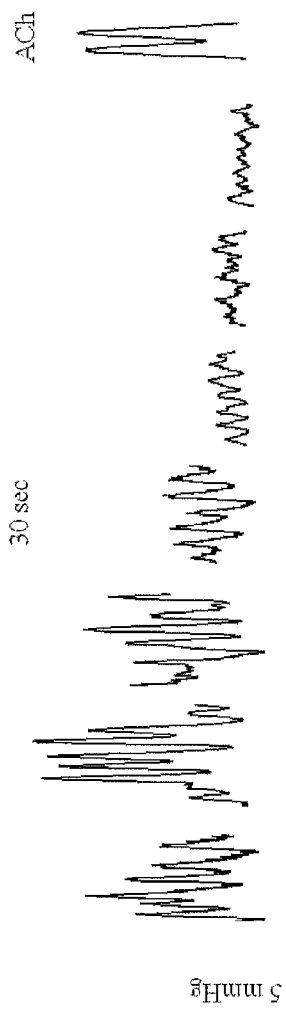
FIGS. 25A and 25B show graphs of intraluminal pressure waveforms during colonic contraction.
Figure 25B:
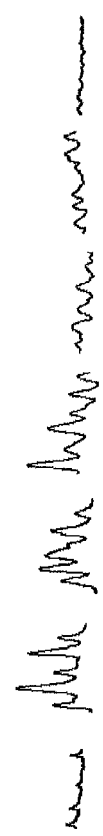
Figure 25C:
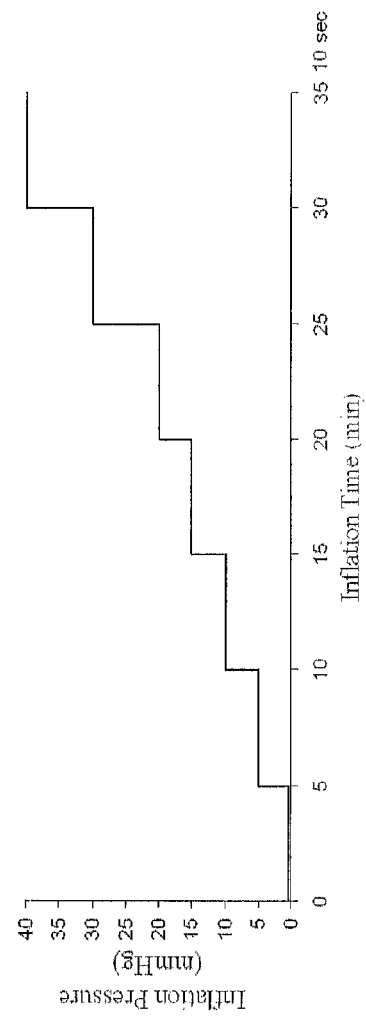
FIG. 25C shows the inflation protocol used to test the stretch-elicited contractility, according to the present disclosure.

The intraluminal pressure waveforms during colonic contraction are shown in FIGS. 25A-25C. FIG. 25A shows in vivo contractile waves, while FIG. 25B shows ex vivo contractile waves. FIG. 25C represents the inflation protocol used to test the stretch-elicited contractility. The amplitudes of intraluminal pressure altered with the inflation pressure. The amplitude reached to maximum in all conditions at 5 mmHg of inflation pressure and suppressed down to minimum when inflation pressure increased up to 50 mmHg.

Figure 26A:
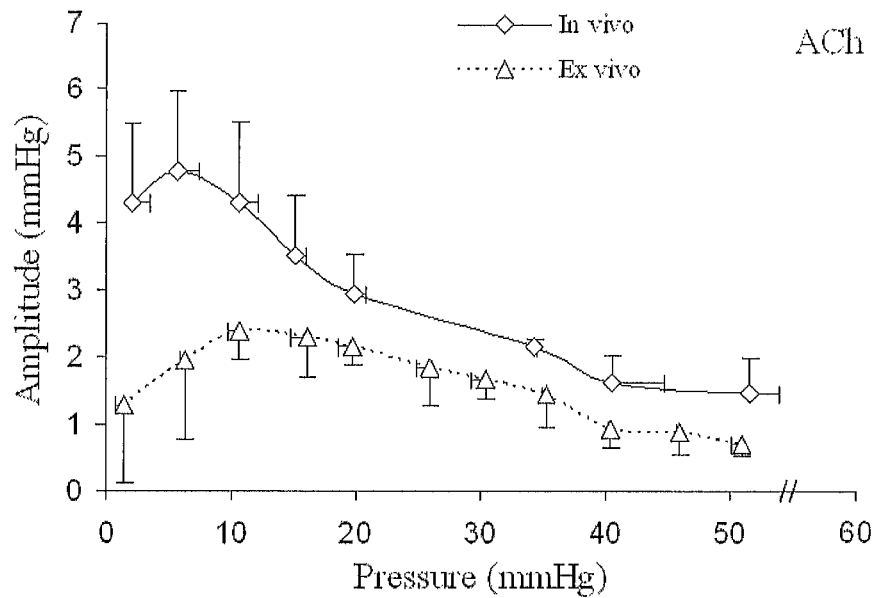
FIGS. 26A and 26B show graphs of amplitude and diameter, respectively, for various conditions, according to the present disclosure.
Figure 26B:
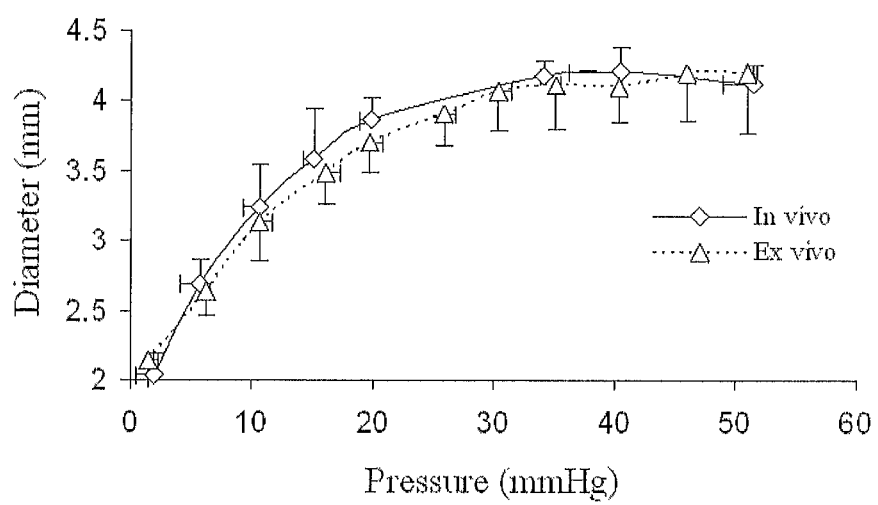

The colonic contractility is shown in FIGS. 26A and 26B as a function of inflation pressure, with FIG. 26A relating to amplitude (in mmHg) and FIG. 26B relating to diameter (in mm). The in-vivo contractility increased from 4.2 mmHg to 4.8 mmHg while the inflation pressure increased from 1 mmHg to 5 mmHg. Then, the colonic contractility decreased significantly down to 1.6 mmHg when the inflation pressure further increased from 5 mmHg to 50 mmHg. The ex-vivo colonic contractility was significantly attenuated in comparison with the in-vivo contractility. The inflation pressure higher than 5 to 10 mmHg may play an inhibitory role in colonic motility. The local neuro-regulation may not be major role since the ex-vivo colonic contractility was significantly lower than the in-vivo contractility. The central nervous regulation largely dominates the colonic contractility. The non-neuroactive contraction stimulated by ACh, however, is still similar to maximum contractility of the in-vivo state, which suggests that neuroactive contraction fails under high distension.

The in-vivo and ex-vivo relationship of inflation pressure and colonic diameter are shown in FIG. 26B, which reflects the circumferential distensibility of the colon. The in-vivo circumferential distensibility was not significantly different to the ex-vivo one ($p>0.05$).

Figure 27A:
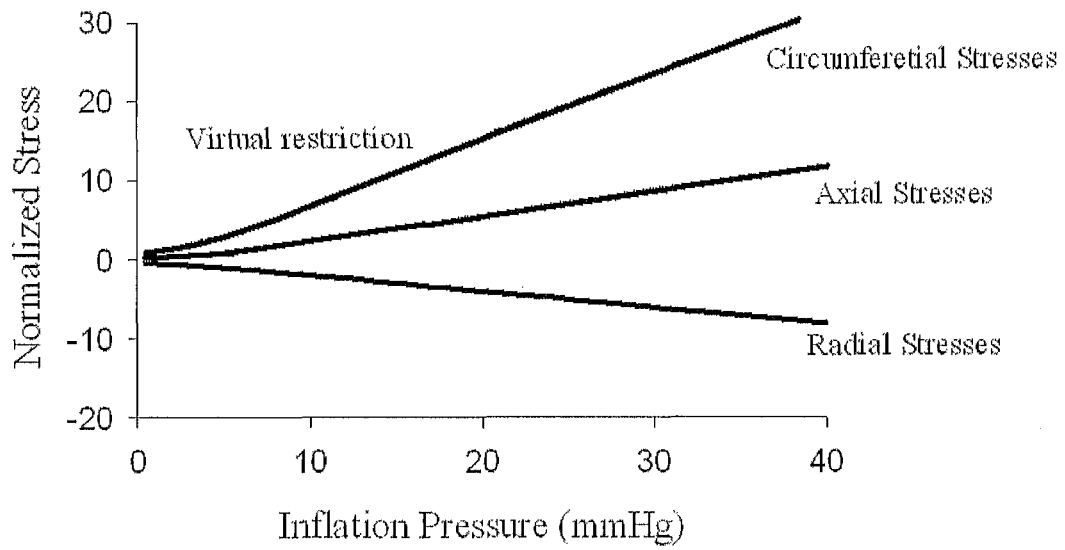
FIGS. 27A and 27B show graphs of the relationship between circumferential, axial, and radial stresses in the intestinal wall in connection with the duodenum and the colon, respectively, according to the present disclosure.
Figure 27B:
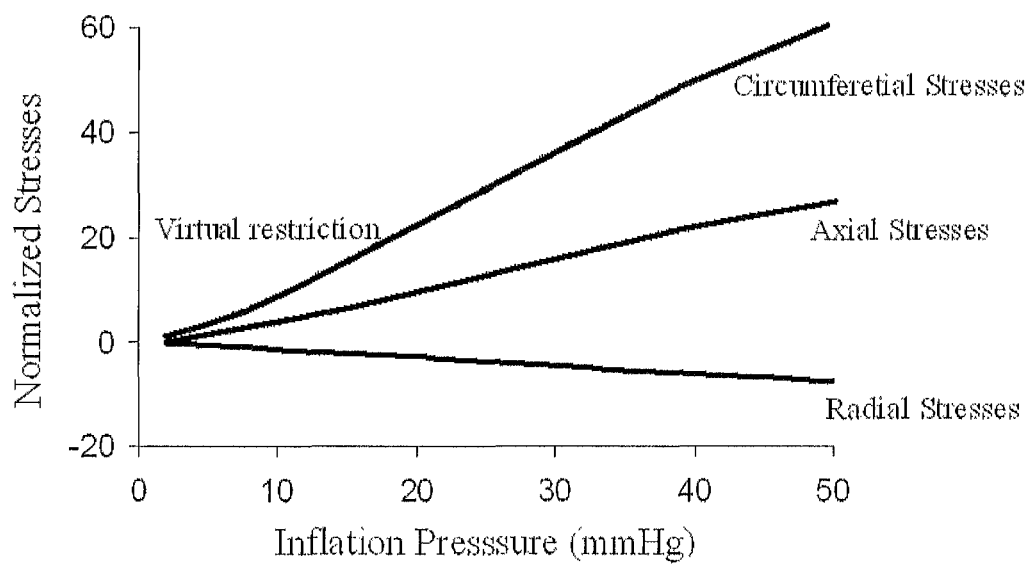

To examine the effect of the stresses on intestinal contractility, the relationship between circumferential, axial, and radial stresses in intestinal wall and inflation pressure were plotted in FIGS. 27A and 27B. FIG. 27A represents data in connection with the duodenum, and FIG. 27B represents data in connection with the colon. Circumferential and axial stresses increased when inflation pressure sent up, which means that the intestine were stretched gradually at circumferential and axial directions, respectively. In addition, radial stress negatively increased when inflation pressure went up, which means that the intestine was compressed gradually.

As referenced above, and in summary, the isovolumic myography system 200 was used to assess intestinal contractility in terms of amplitude of the variation of intraluminal pressure. The in-vivo preparation was designed to detect the efferent neurogenic contraction that efferent fibers were intact, and the ex-vivo preparation was designed to measure the efferent-independent (local regulatory) contraction that the efferent nervous signals were eliminated. The in-vivo duodenal contractile amplitude is a little larger than that in ex-vivo state, indicating that local regulatory signal contributes the contractility. The in-vivo colonic contractile amplitude is significantly larger than that in ex-vivo state, indicating that efferent neurogenic signal contributes the contractility. The variation of circumferential, axial, and radial stresses in intestinal wall were analyzed to examine the role of the stresses in the inhibition of intestinal contractility.

Intestinal contractility is closely correlated to the mechanosensor located in the intestinal wall. The myogenic response of intestinal smooth muscle and efferent neurogenic contraction are regulated by mechanosensors, namely the afferent vagus nerve and the efferent vagus nerve. The relation between afferent vagus signals and intestinal distension was identified decades ago, noting that the mechanosensors in the intestinal wall are primary sensors of mechanical stimulation. The efferent (motor) vagus signals are responses of central nervous system to the afferent (sensory) vagus stimulation.

Intestinal motility is regulated by the extrinsic nervous system (parasympathetic and sympathetic nervous systems) and the intrinsic nervous system. The intrinsic nervous system is structurally different in the colon than in the small intestine. The contraction and motility of colonic cells are more dependent on the extrinsic nervous system for regulation than in the small intestine. One of the physiological functions of efferent vagus signals is to regulate the intestinal contractility, as the intestinal contractility reflects the activation of efferent vagus nerve.

As referenced herein, intestinal contractility was evaluated in an ex-vivo preparation which excludes efferent vagus regulation. In the ex-vivo intestine, the nerve fibers are excised and damaged, and hence there is a loss of efferent vagus signals which appears to be significant for mechanical distension-induced contractility. The ex-vivo colonic contractility of intestinal smooth muscle was significantly attenuated due to the absence of efferent vagus signals. The strong in-vivo contractility reflects the efferent vagus activation in response to mechanical stimulation which is sensed by afferent vagus nerves, which implies that the contractility is regulated by the central nervous system.

Distension has been confirmed as a stimulator of intestinal afferent sensors. The afferent nerve is excited to very high level in response to inflation, which establishes the sensory and transmission to central nervous system. This is the first part of gut-brain cross-talk and the second part is the signal from central nervous system to control the intestinal function. The in-vivo intestinal contractility measured by an exemplary isovolumic myograph of the present disclosure, a parameter of motility, virtually reflects the resultant of gut-brain cross-talk on motility, which indicates the final action of afferent sensory→central nervous system→efferent action signal final action (function, motility, etc). Since the distension excited afferent signal is well established, the results referenced in the present disclosure indicate that the efferent signal may be parasympathetic excitation to attenuate the intestinal motility.

Furthermore, it is noted that the efferent vagus (motor) inactivation may occur after abdominal surgery, postoperative intestinal ileus. Ileus is the failure of the gastrointestinal tract to provide timely, aboral movements of air and chyme from esophagus to the anus. The intestinal ileus (obstruction) may be mediated by central neural influences, neurologic reflex (sensitive afferent nerves) response, the disturbances of myoelectrical activity, humoral responses, and local or regional activation of immune system function. The weakening or loss of intestinal motility is the significant character of intestinal ileus. In the studies referenced herein, the results implied that the central nervous system and the neurologic reflex response involved in the decrease in intestinal contractility. The humoral response and the immune system may not involve in the mediation of the acute decrease in intestinal contractility.

An exemplary isovolumic myograph of the present disclosure (system 200) was used to evaluate the intestinal globe contractility, and is therefore suitable to understand the effect of stimulations of inflation pressure on intestinal contraction. Although the regional contraction was not measured with such an isovolumic myograph during the aforementioned study, the efferent vagus activation was evaluated by the intestinal contractility with the isovolumic myograph. In conclusion, the various isovolumic myographs (systems 200) of the present disclosure facilitates the understanding of intestinal contractility in response to mechanical stimulation. The in-vivo and ex-vivo intestinal contractility in response to inflation pressure provides evidence that intestinal motility can be regulated by central nervous system and local nervous regulation.

While various embodiments of isovolumic myograph systems and methods for using the same have been described in considerable detail herein, the embodiments are merely offered by way of non-limiting examples of the disclosure described herein. It will therefore be understood that various changes and modifications may be made, and equivalents may be substituted for elements thereof, without departing from the scope of the disclosure. Indeed, this disclosure is not intended to be exhaustive or to limit the scope of the disclosure.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. Other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

We claim:

1. A system for detecting a luminal organ response to mechanical stimulation, the system comprising:
    a first conduit and a second conduit each having a proximal end, a distal end, and a lumen therethrough, the distal ends each sized and shaped to fit within a luminal organ and configured to maintain the luminal organ at a first length within a chamber for receiving a fluid and the luminal organ;
    a pressure transducer in communication with at least one of the first conduit and the second conduit and configured to measure an internal pressure within the luminal organ; and
    a volume compensator coupled to the first conduit and operable to inject a liquid into the luminal organ so that the liquid increases the internal pressure within the luminal organ in response to a decrease in the internal pressure within the luminal organ as identified by the pressure transducer and to maintain at or near an isovolumic state within the luminal organ;
    wherein the system is configured so that the luminal organ is closed to axial flow conditions therethrough;
    wherein the system is operable to measure a change to the internal pressure within the luminal organ resulting from a luminal organ response; and
    wherein, when the internal pressure is at or near an established set point, the volume compensator does not automatically remove fluid from the luminal organ in response to an increase in the internal pressure.

2. The system of claim 1, further comprising:
    the chamber for receiving the fluid and the luminal organ.

3. The system of claim 2, further comprising:
    a first retaining device positioned at least partially within the chamber, the first retaining device capable of retaining the luminal organ positioned therein at the first length wherein the first conduit is coupled to the first retaining device; and
    a second conduit coupled to a second retaining device positioned at least partially within the chamber.

4. The system of claim 3, wherein when the luminal organ is retained therein, the system is operable to facilitate detection of a response of the luminal organ to one or more chemicals in contact with the luminal organ.

5. The system of claim 4, wherein the one or more chemicals are introduced into the chamber.

6. The system of claim 4, wherein the one or more chemicals are introduced into a lumen of the luminal organ via at least one of the first conduit and the second conduit.

7. The system of claim 3, wherein the volume compensator comprises a syringe.

8. The system of claim 4, further comprising:
a device capable of detecting a physical change to the luminal organ.

9. The system of claim 8, wherein the device is selected from the group consisting of a camera, a pressure transducer, and a microscope.

10. The system of claim 3, wherein the first retaining device comprises a first retaining wall and wherein the second retaining device comprises a second retaining wall.

11. The system of claim 3, wherein the volume compensator comprises at least one pressurized vessel.

12. The system of claim 11, further comprising:
a pressure regulator in communication with the at least one pressurized vessel, the pressure regulator capable of regulating a vessel pressure.

13. The system of claim 3, wherein when a quantity of the liquid is present within the luminal organ to form an initial internal pressure, the volume compensator is operable to inject additional liquid into the luminal organ in response to the decrease in the initial internal pressure within the luminal organ due to transport of an amount of the liquid across a wall of the luminal organ, so as to increase the internal pressure within the luminal organ to or near the initial internal pressure and maintain at or near an isovolumic state therein.

14. The system of claim 1, wherein the volume compensator does not automatically remove fluid from the luminal organ in response to the increase in the internal pressure resulting from the luminal organ response.

15. The system of claim 2, wherein when a quantity of the liquid is present within the luminal organ to form an initial internal pressure, the volume compensator is operable to inject additional liquid into the luminal organ in response to the decrease in the initial internal pressure within the luminal organ due to transport of an amount of the liquid across a wall of the luminal organ, so as to increase the internal pressure within the luminal organ to or near the initial internal pressure and maintain at or near an isovolumic state therein.

16. The system of claim 14, wherein the volume compensator comprises at least one pressurized vessel, the system further comprising:
a pressure regulator in communication with the at least one pressurized vessel, the pressure regulator capable of regulating a vessel pressure.

17. The system of claim 1, wherein the luminal organ is selected from the group consisting of a stomach, a trachea, a lymph vessel, a lymph duct, a urinary bladder, a ureter, a gall bladder, a bile duct, a hepatic duct, and an intestine.

18. The system of claim 17, wherein the distal end of the first conduit is positioned within an incision of the stomach so that the lumen of the first conduit is in fluid communication with a lumen of the stomach.

19. The system of claim 1, wherein the distal end of the first conduit is positioned within an incision of the luminal organ while the luminal organ is present within a living mammal so that the lumen of the first conduit is in fluid communication with a lumen of the luminal organ.

20. The system of claim 1, wherein when the distal end of the first conduit is positioned within the luminal organ, the system is operable to detect a response of the luminal organ to an increase in the internal pressure of the luminal organ.

21. The system of claim 20, further comprising:
the chamber for receiving the fluid and the luminal organ;
wherein when a chemical is introduced into the chamber, the system is further configured to detect a parameter change of the luminal organ in response to the chemical.

22. The system of claim 1, wherein the volume compensator comprises a syringe.

23. The system of claim 1, further comprising:
a device capable of detecting a physical change to the luminal organ, the device selected from the group consisting of a camera and a microscope.

24. A system for detecting a luminal organ response to mechanical stimulation, the system comprising:
a chamber for receiving a fluid and a mammalian luminal organ;
a first conduit and a second conduit each having a proximal end, a distal end, and a lumen therethrough, the distal ends each sized and shaped to fit within the mammalian luminal organ and configured to maintain the mammalian luminal organ at a first length within the chamber;
a pressure transducer in communication with at least one of the first conduit and the second conduit and configured to measure an internal pressure within the mammalian luminal organ; and
a volume compensator coupled to the first conduit, wherein when a quantity of a liquid is present within the mammalian luminal organ to form an initial internal pressure, the volume compensator is operable to inject additional liquid into the mammalian luminal organ to maintain a substantially isovolumic state within the luminal organ in response to a decrease in the initial internal pressure as identified by the pressure transducer and due to transport of an amount of the liquid across a wall of the mammalian luminal organ, so as to increase an internal pressure within the mammalian luminal organ to at or near the initial internal pressure;
wherein the system is configured so that the mammalian luminal organ is closed to axial flow conditions therethrough; and
wherein, when the initial internal pressure is at or near an established set point, the volume compensator does not automatically remove fluid from the luminal organ in response to an increase in the internal pressure within the mammalian luminal organ.

25. The system of claim 24, wherein the system is operable to measure a change to the internal pressure within the luminal organ resulting from a luminal organ response.

* * * * *